US012567486B2

(12) United States Patent
Sunder et al.

(10) Patent No.: US 12,567,486 B2
(45) Date of Patent: Mar. 3, 2026

(54) MULTI-MODEL MACHINE LEARNING ARCHITECTURE FOR FILTERING ENTITY PROFILES

(71) Applicant: ZS Associates, Inc., Evanston, IL (US)

(72) Inventors: Arrvind Sunder, Chicago, IL (US); Siddharth Kumar, Robbinsville, NJ (US); KrishnaKalyan A, Philadelphia, PA (US); Gloria Zhou, San Jose, CA (US); Sambit Nandi, Maharashtra (IN); Geetanjali Mishra, Karnataka (IN); Saurabh Sohlot, Delhi (IN); Asheesh Shukla, Lower Gwynedd, PA (US)

(73) Assignee: ZS Associates, Inc.

( * ) Notice: Subject to any disclaimer, the term of this patent is extended or adjusted under 35 U.S.C. 154(b) by 86 days.

(21) Appl. No.: 18/436,188

(22) Filed: Feb. 8, 2024

(65) Prior Publication Data

US 2024/0274247 A1 Aug. 15, 2024

(51) Int. Cl.
*G16H 10/60* (2018.01)
(52) U.S. Cl.
CPC .................................. *G16H 10/60* (2018.01)
(58) Field of Classification Search
CPC ...... G06Q 10/105; G06Q 30/02; G06Q 50/22; G06Q 10/06398; G06Q 50/01; G06Q 2220/00; G16H 10/60; G16H 50/70
USPC ............................................................. 705/3
See application file for complete search history.

(56) References Cited

U.S. PATENT DOCUMENTS

2009/0222551 A1* 9/2009 Neely ................... G06F 16/951
709/224
2021/0050086 A1* 2/2021 Rose ..................... G16H 20/30

* cited by examiner

*Primary Examiner* — Igor N Borissov
(74) *Attorney, Agent, or Firm* — Foley & Lardner LLP

(57) ABSTRACT

Disclosed herein are methods and systems for filtering entity profiles. A method includes receiving, from a plurality of data sources and for a plurality of medical entities, clinical data and online interaction data; generating a plurality of entity profiles for the plurality medical entities; calculating one or more clinical metrics and one or more online interaction metrics for the plurality of entity profiles from the clinical data and the online interaction data; executing a model using identifications of the plurality of entity profiles and the one or more clinical metrics and the one or more online interaction metrics as input to generate influence scores for the plurality of entity profiles; selecting a subset of the plurality of entity profiles responsive to each entity profile of the subset having an influence score satisfying a selection criteria; and generating a record comprising identifications of the subset of the plurality of entity profiles.

20 Claims, 15 Drawing Sheets

100

160

Client
165A

Client
165B

Client
165N

Network
170

Software 180

Platform 185

Infrastructure 190

Server 195

Cloud
175

170B

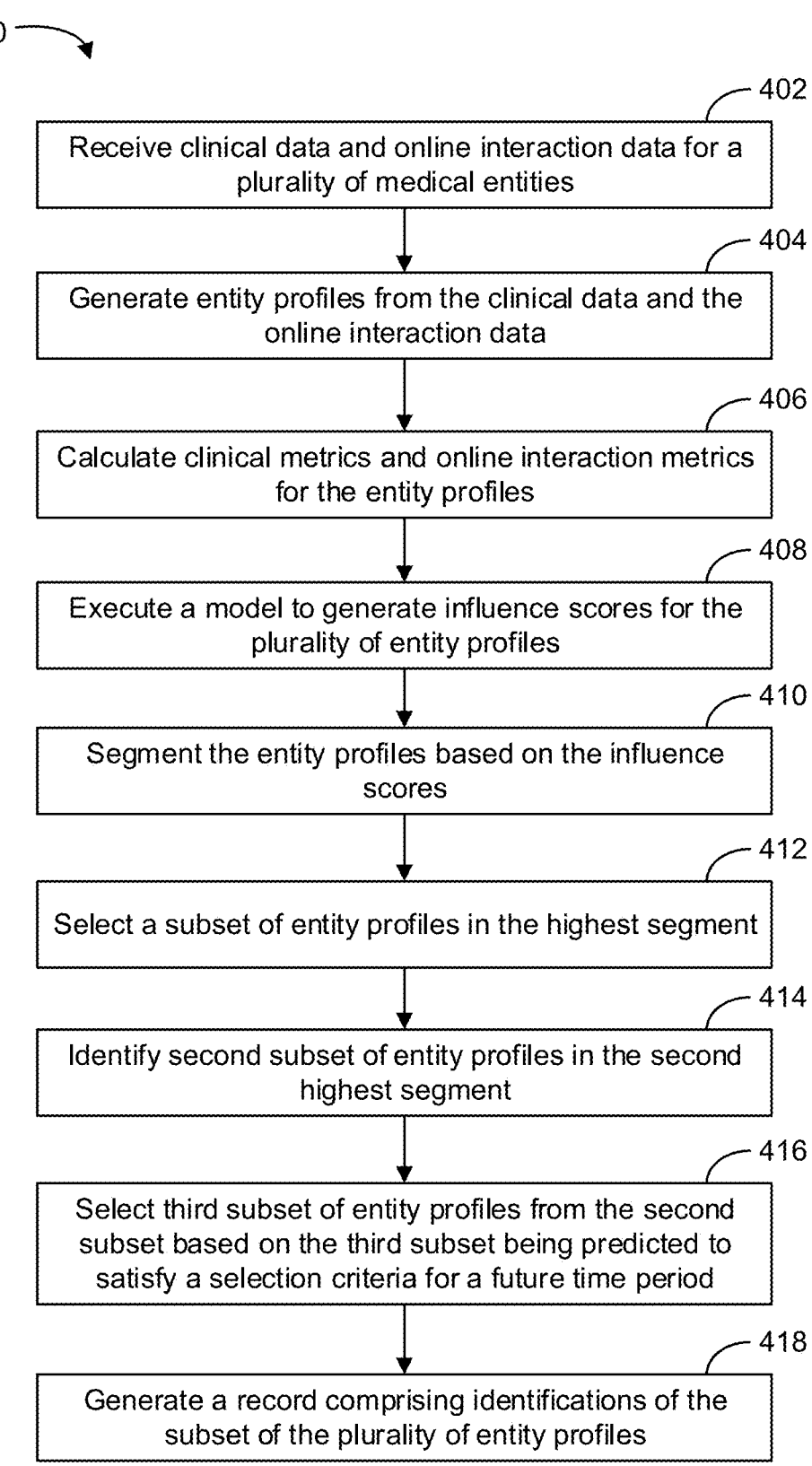

400

402
Receive clinical data and online interaction data for a plurality of medical entities 404
Generate entity profiles from the clinical data and the online interaction data 406
Calculate clinical metrics and online interaction metrics for the entity profiles 408
Execute a model to generate influence scores for the plurality of entity profiles 410
Segment the entity profiles based on the influence scores 412
Select a subset of entity profiles in the highest segment 414
Identify second subset of entity profiles in the second highest segment 416
Select third subset of entity profiles from the second subset based on the third subset being predicted to satisfy a selection criteria for a future time period 418
Generate a record comprising identifications of the subset of the plurality of entity profiles

MULTI-MODEL MACHINE LEARNING ARCHITECTURE FOR FILTERING ENTITY PROFILES

CROSS-REFERENCE TO RELATED APPLICATIONS

This application claims the benefit of priority to Indian Provisional Application No. 202341008389, filed Feb. 9, 2023, the entirety of which is incorporated by reference herein.

TECHNICAL FIELD

This application relates generally to implementing a multi-model machine learning architecture for filtering entity profiles.

BACKGROUND

Filtering profiles based on their influence within a particular community is a historically analogue process. For example, conventionally, a company may seek to identify individuals that have an online presence based on the company learning about the individual or based on a publication the individual wrote. The company may also seek to identify individuals based on other metrics (e.g., research activities, leadership engagement, patient management, and industry engagement). Doing so may require desk research, which can be time consuming and inefficient. For example, the company may identify a few of the individual's posts and determine the individual has a large influence based on a few subjective metrics, such as the amount of engagement the individual's posts generate and/or the quality of the individual's posts. However, given the large number of individuals that interact with each other online and the variety of topics about which any single individual can post, it can be difficult to filter out individuals that have the most online influence. The difficulty may only increase for forward-thinking companies seeking to identify individuals that do not have a strong online presence now, but may have one in the future. Not only is identifying such individuals in this manner tedious, time-consuming, and expensive, it often results in influential individuals being missed and/or individuals being falsely identified as influential as a result of only having a small subset of data.

During the past several years, drug developers in the public and private sectors have expressed keen interest in addressing this problem by selectively identifying influential individuals and individuals that may be influential in the future. To do so, the drug developers may identify companies that research in the same areas as the developers and perform an online search of the companies' employees or researchers. In doing so, the drug developers may identify the individuals that are employed by these companies from a database and perform an online query using their names. While this method may produce some results, given the vast online community and the amount of data that is available online and stored in various databases or data sources, the method may result in the drug developers not analyzing data from online or other community members or discarding data from members that facially appear to not be influential.

SUMMARY

For the aforementioned reasons, there is a need to take advantage of the breadth of information that is transmitted over the Internet and between different types of data sources (e.g., publicly available data sources, medical data sources, medical data sources combined with desk research and/or human intelligence, etc.) to identify influential and future influential community members. More specifically, because the data that is available to help identify influential and future influential community members is available over the Internet, there is a need to develop an improved search engine of computer models (e.g., machine learning and/or optimization models) that can automatically quantify and generate a meaningful output identifying the influential and future influential members using such data.

A system implementing the systems and methods described herein may overcome the aforementioned technical deficiencies by providing a series of individually trained computer models to select influential medical entities (e.g., key opinion leaders or KOLs) and/or future influential medical entities (e.g., rising stars). For example, in some implementations, a processor of such a system may collect different types of data (e.g., research data, open payments data, leadership (desk research) data, social media presence data, patients managed (Claims) that was generated by or otherwise associated with entities in the medical field. Using the collected data, the processor may generate a network graph data structure that includes profiles (or nodes) with edges between each other indicating relationships (e.g., connections) between the entities in the medical field (e.g., one researcher may have worked and/or co-authored a publication with another researcher). The processor may calculate clinical metrics and/or research metrics from clinical data such as publications, Congress Abstracts, or clinical trials that the different medical entities conducted. The processor may additionally calculate online interaction metrics from the online interaction data the processor collects from servers that host various websites. The processor may feed the relationships of the network data structure and the metrics into one or more models to calculate influence scores for the profiles of the network graph data structure. By using metrics instead of the data itself, the processor may format the data into a format readable by the model (which may be helpful when the data involves text instead of numbers) and minimize the amount of data that needs to be used to determine or select the most influential profiles. After using the model to calculate influence scores for various profiles, the processor may feed the scores into a filtering algorithm to segment the profiles into groups according to the scores. The processor may identify the profiles that correspond to the segment or group with the highest influence score as the most influential profiles. The processor may then generate a record comprising identifications of the selected profiles indicating the profiles are associated with the most influential medical entities. Thus, the processor may operate to use an improved search engine to identify and filter results of profiles that satisfy influence score-based criteria using the network graph data structure.

In some cases, the processor may identify the rising stars from the profiles based on their influence scores. A rising star may be a medical entity that does not meet an influence threshold at the time of the processing, but that is predicted to do so in the future. For example, a rising star may be a relatively young health care provider or an emerging key opinion leader, as described herein. The processor may identify the rising stars by first identifying the profiles that are associated with the second highest segment or group of influence scores. The processor may retrieve clinical and/or online interaction data from a defined recent time period for the identified profiles. The clinical data may include data such as research data, open payments data, leadership (e.g., desk research) data, social media presence data, patients managed (Claims) data, etc. The processor may calculate metrics based on the retrieved data and feed the metrics into a time series-based forecast algorithm to predict future influence scores for the profiles. The processor may compare the future influence scores to a threshold used to identify the most influential profiles and determine if the future influence scores exceed the threshold. The processor may identify profiles as being associated with rising stars responsive to the future influence scores exceeding the threshold. In this way, the processor may use a series of models to both identify medical entities that are the most influential now and medical entities that are predicted to be influential in the future.

In an embodiment, a method comprises receiving, by a processor from a plurality of data sources and for a plurality of medical entities, clinical data and online interaction data; generating, by the processor from the clinical data and the online interaction data, a plurality of entity profiles for the plurality medical entities; calculating, by the processor, one or more clinical metrics and one or more online interaction metrics for the plurality of entity profiles from the clinical data and the online interaction data; executing, by the processor, a model using identifications of the plurality of entity profiles and the one or more clinical metrics (e.g., research metrics, open payments metrics, leadership (desk research) metrics, social media presence metrics, patients managed (claims) metrics) and the one or more online interaction metrics as input to generate influence scores for the plurality of entity profiles; selecting, by the processor, a subset of the plurality of entity profiles responsive to each entity profile of the subset having an influence score satisfying a selection criteria; and generating, by the processor, a record comprising identifications of the subset of the plurality of entity profiles.

In another embodiment, a system comprises a server comprising a processor and a non-transitory computer-readable medium. The non-transitory computer-readable medium may contain instructions that when executed by the processor causes the processor to perform operations comprising receiving, from a plurality of data sources and for a plurality of medical entities, clinical data and online interaction data; generating, from the clinical data and the online interaction data, a plurality of entity profiles for the plurality medical entities; calculating one or more clinical metrics and one or more online interaction metrics for the plurality of entity profiles from the clinical data and the online interaction data; executing a model using identifications of the plurality of entity profiles and the one or more clinical metrics and the one or more online interaction metrics as input to generate influence scores for the plurality of entity profiles; selecting a subset of the plurality of entity profiles responsive to each entity profile of the subset having an influence score satisfying a selection criteria; and generating a record comprising identifications of the subset of entity profiles.

BRIEF DESCRIPTION OF THE DRAWING FIGURES

Objects, aspects, features, and advantages of embodiments disclosed herein will become more fully apparent from the following detailed description, the appended claims, and the accompanying drawing figures in which reference numerals identify similar or identical elements. Reference numerals that are introduced in the specification in association with a drawing figure may be repeated in one or more subsequent figures without additional description in the specification to provide context for other features, and not every element may be labeled in every figure. The drawing figures are not necessarily to scale, emphasis instead being placed upon illustrating embodiments, principles, and concepts. The drawings are not intended to limit the scope of the claims included herewith.

FIG. 4 illustrates a flowchart of an example method for implementing a multi-model architecture for filtering entity profiles, in accordance with one or more implementations;

Figure 9A:
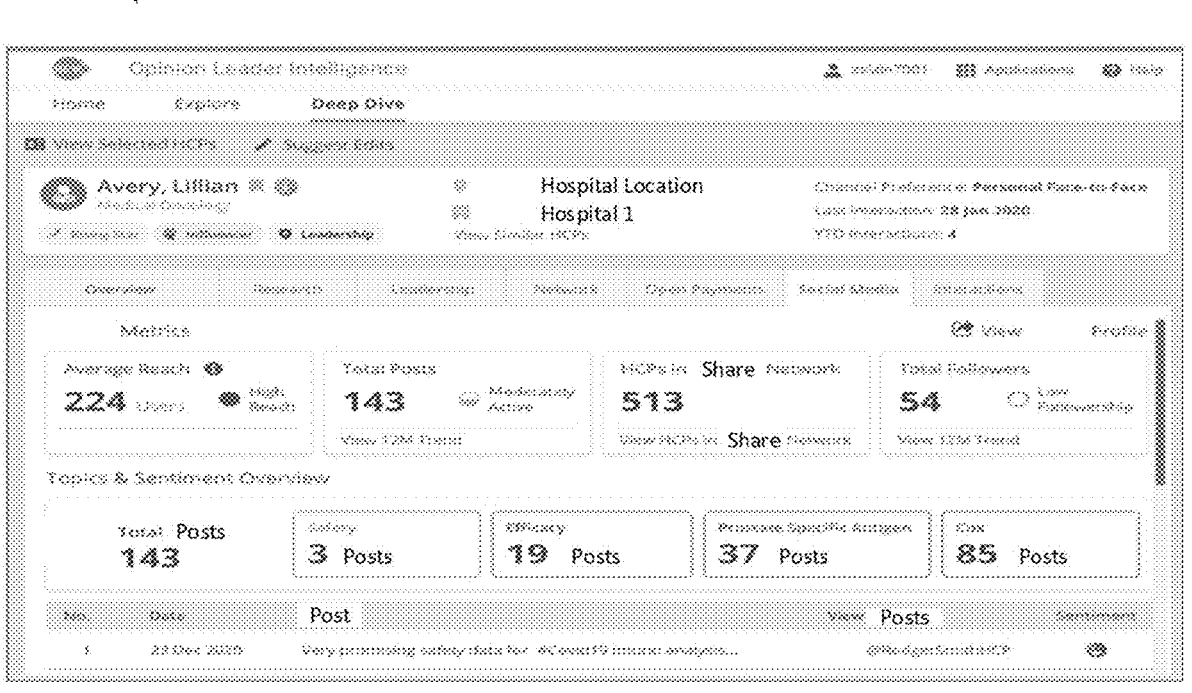
Figure 9B:
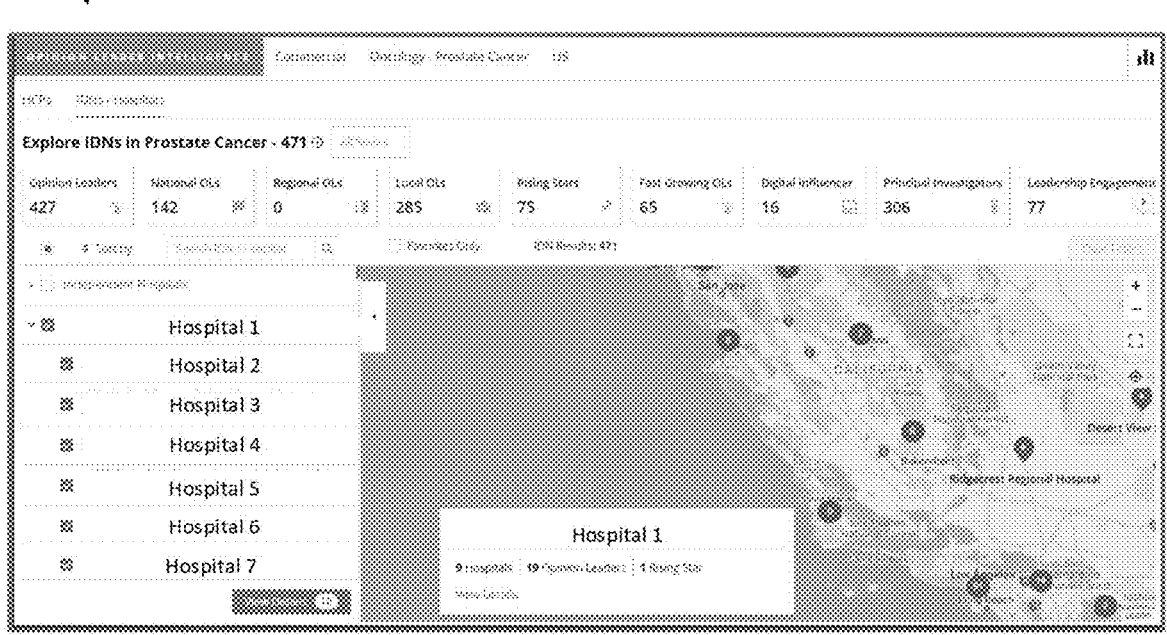
Figure 9C:
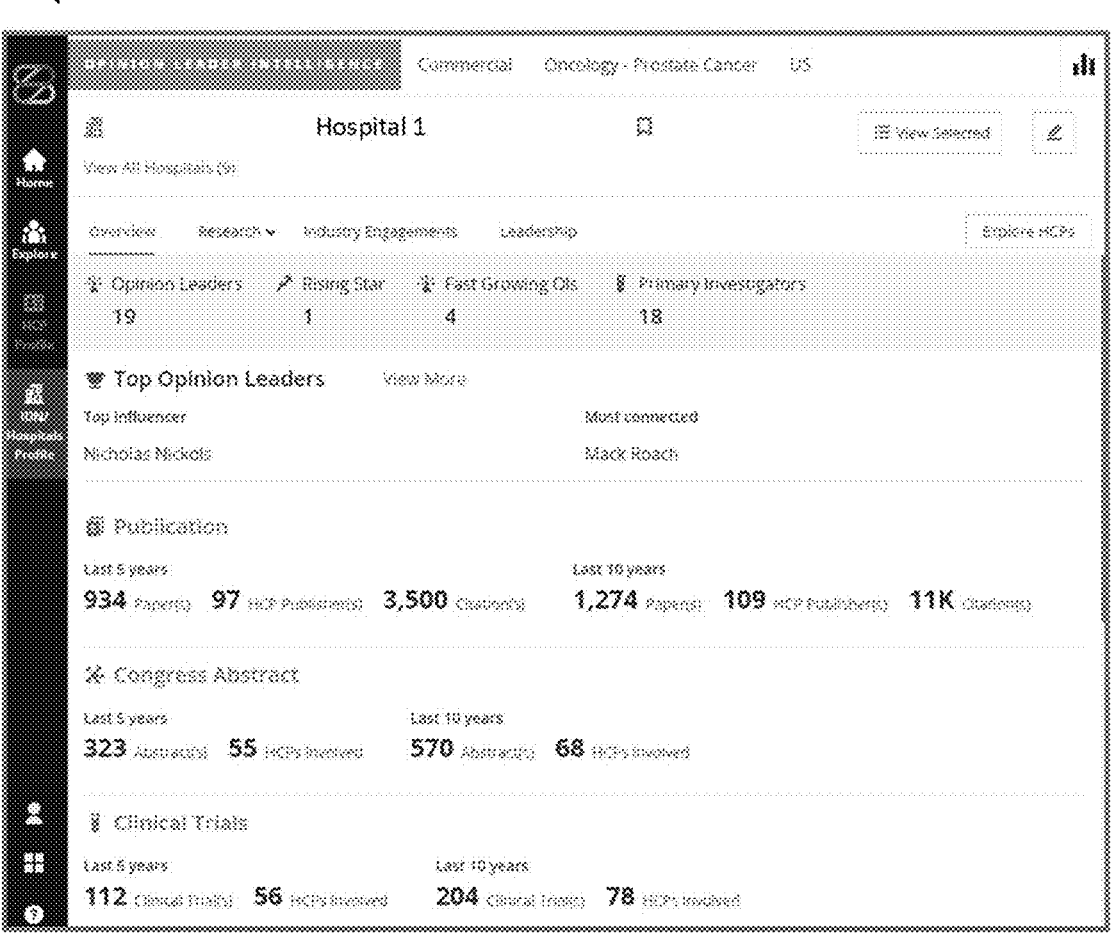

FIGS. 8A-D illustrate a non-limiting example of a data flow of a system implementing the systems and methods described herein, in accordance with one or more implementations; and FIGS. 9A-9C illustrate non-limiting examples of graphical user interfaces of an electronic platform enabling users to request and view details regarding key opinion leaders and/or rising stars, in accordance with one or more implementations.

The features and advantages of the present solution will become more apparent from the detailed description set forth below when taken in conjunction with the drawings, in which like reference characters identify corresponding elements throughout. In the drawings, reference numbers generally indicate identical, functionally similar, and/or structurally similar elements.

DETAILED DESCRIPTION

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

Section A describes a computing environment that may be useful for practicing embodiments described herein;

Section B describes a non-limiting example of a multi-model entity profile filtering system architecture; and Section C describes a non-limiting example of a method for implementing a multi-model system architecture to filter entity profiles.

Section A: Computing Environment

Prior to discussing the specifics of embodiments of the systems and methods of an appliance and/or client, it may be helpful to discuss the computing environments in which such embodiments may be deployed.

Figure 1A:
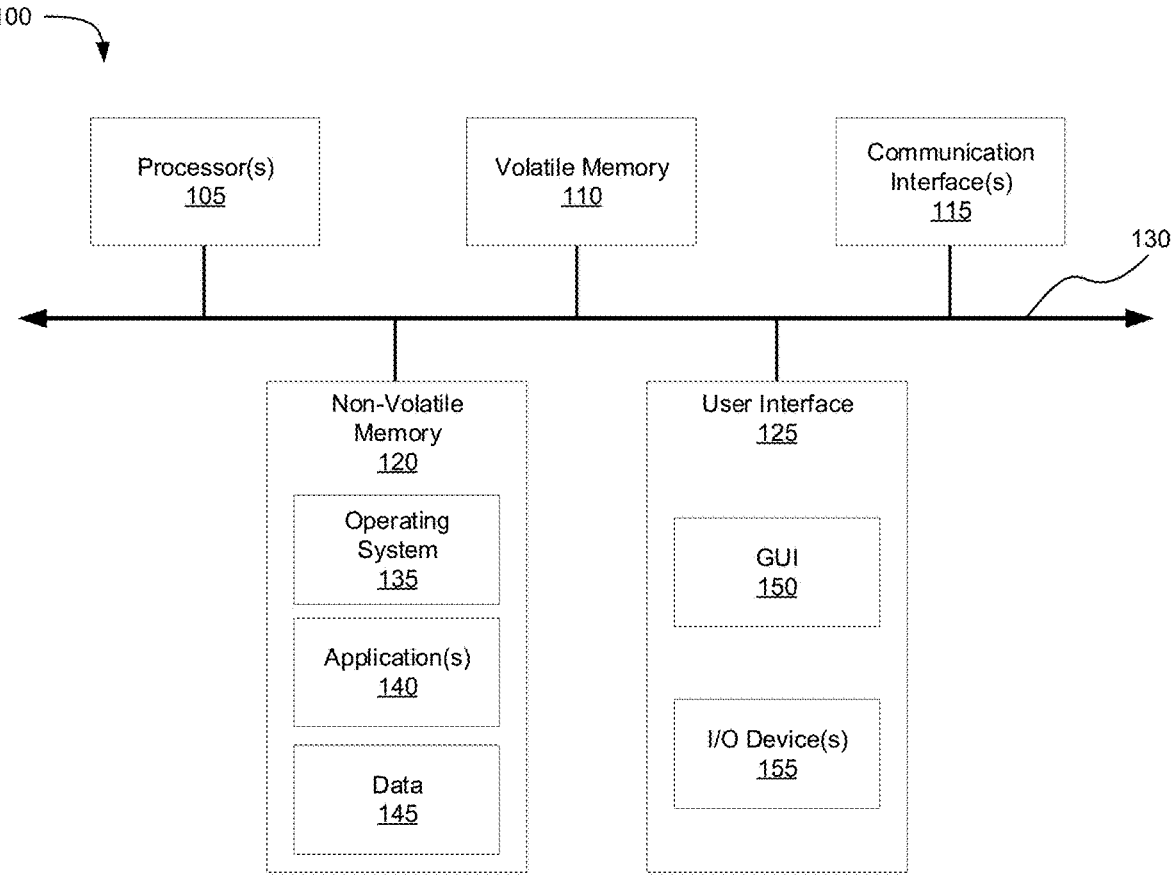
FIG. 1A is a block diagram of embodiments of a computing device.

As shown in FIG. 1A, computer 100 may include one or more processors 105, volatile memory 110 (e.g., random access memory (RAM)), non-volatile memory 120 (e.g., one or more hard disk drives (HDDs) or other magnetic or optical storage media, one or more solid-state drives (SSDs) such as a flash drive or other solid-state storage media, one or more hybrid magnetic and solid-state drives, and/or one or more virtual storage volumes, such as cloud storage, or a combination of such physical storage volumes and virtual storage volumes or arrays thereof), a user interface (UI) 125, one or more communications interfaces 115, and a communication bus 130. User interface 125 may include a graphical user interface (GUI) 150 (e.g., a touchscreen, a display, etc.) and one or more input/output (I/O) devices 155 (e.g., a mouse, a keyboard, a microphone, one or more speakers, one or more cameras, one or more biometric scanners, one or more environmental sensors, one or more accelerometers, etc.). The non-volatile memory 120 stores operating system 135, one or more applications 140, and data 145 such that, for example, computer instructions of operating system 135 and/or applications 140 are executed by processor(s) 105 out of volatile memory 110. In some embodiments, volatile memory 110 may include one or more types of RAM and/or a cache memory that may offer a faster response time than the main memory. Data may be entered using an input device of GUI 150 or received from I/O device(s) 155. Various elements of computer 100 may communicate via one or more communication buses, shown as communication bus 130.

Computer 100 as shown in FIG. 1A is shown merely as an example, as clients, servers, intermediary, and other networking devices and may be implemented by any computing or processing environment and with any type of machine or set of machines that may have suitable hardware and/or software capable of operating as described herein. Processor(s) 105 may be implemented by one or more programmable processors to execute one or more executable instructions, such as a computer program, to perform the functions of the system. As used herein, the term "processor" describes circuitry that performs a function, an operation, or a sequence of operations. The function, operation, or sequence of operations may be hardcoded into the circuitry or soft coded by way of instructions held in a memory device and executed by the circuitry.

A "processor" may perform the function, operation, or sequence of operations using digital values and/or using analog signals. In some embodiments, the "processor" can be embodied in one or more application-specific integrated circuits (ASICs), microprocessors, digital signal processors (DSPs), graphics processing units (GPUs), microcontrollers, field-programmable gate arrays (FPGAs), programmable logic arrays (PLAs), multi-core processors, or general-purpose computers with associated memory. The "processor" may be analog, digital or mixed-signal. In some embodiments, the "processor" may be one or more physical processors or one or more "virtual" (e.g., remotely located or "cloud") processors. A processor including multiple processor cores and/or multiple processors may provide functionality for parallel, simultaneous execution of instructions, or for parallel, simultaneous execution of one instruction on more than one piece of data.

Communications interfaces 115 may include one or more interfaces to enable computer 100 to access a computer network such as a Local Area Network (LAN), a Wide Area Network (WAN), a Personal Area Network (PAN), or the Internet through a variety of wired and/or wireless or cellular connections.

In described embodiments, the computer 100 may execute an application on behalf of a user of a client computer. For example, the computer 100 may execute a virtual machine, which provides an execution session within which applications execute on behalf of a user or a client computer, such as a hosted desktop session. The computer 100 may also execute a terminal services session to provide a hosted desktop environment. The computer 100 may provide access to a computing environment including one or more of one or more applications, one or more desktop applications, and one or more desktop sessions in which one or more applications may execute.

Figure 1B:
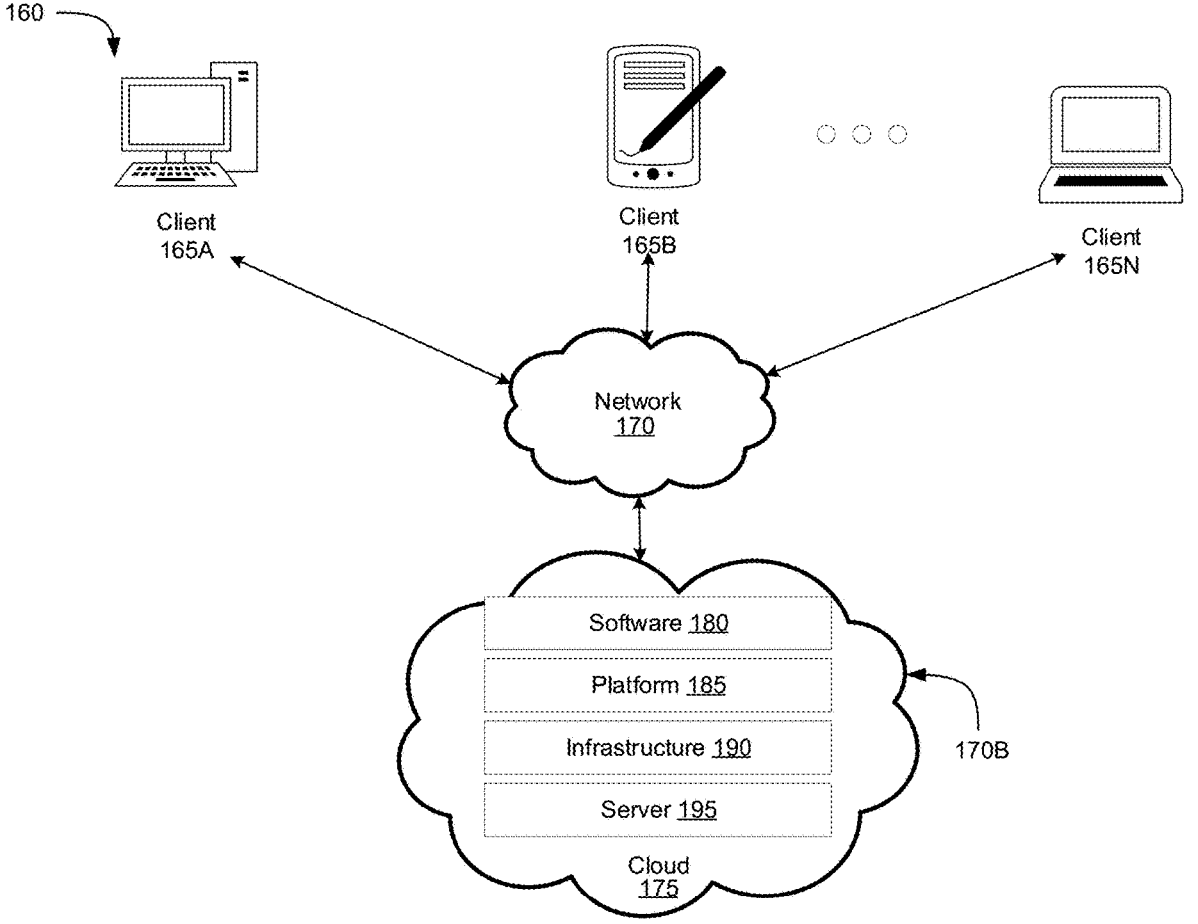
FIG. 1B is a block diagram depicting a computing environment comprising client devices in communication with cloud service providers.

Referring to FIG. 1B, a computing environment 160 is depicted. Computing environment 160 may generally be implemented as a cloud computing environment, an on-premises ("on-prem") computing environment, or a hybrid computing environment including one or more on-prem computing environments and one or more cloud computing environments. When implemented as a cloud computing environment, also referred to as a cloud environment, cloud computing, or cloud network, computing environment 160 can provide the delivery of shared services (e.g., computer services) and shared resources (e.g., computer resources) to multiple users. For example, the computing environment 160 can include an environment or system for providing or delivering access to a plurality of shared services and resources to a plurality of users through the internet. The shared resources and services can include but are not limited to, networks, network bandwidth, servers, processing, memory, storage, applications, virtual machines, databases, software, hardware, analytics, and intelligence.

In some embodiments, the computing environment 160 may provide client 165 with one or more resources provided by a network environment. The computing environment 160 may include one or more clients 165a-165n, in communication with a cloud 175 over one or more networks 170. Clients 165 may include, e.g., thick clients, thin clients, and zero clients. The cloud 108 may include back-end platforms, e.g., servers, storage, server farms, or data centers. The clients 165 can be the same as or substantially similar to computer 100 of FIG. 1A.

The users or clients 165 can correspond to a single organization or multiple organizations. For example, the computing environment 160 can include a private cloud serving a single organization (e.g., enterprise cloud). The computing environment 160 can include a community cloud or public cloud serving multiple organizations. In some embodiments, the computing environment 160 can include a hybrid cloud that is a combination of a public cloud and a private cloud. For example, the cloud 175 may be public, private, or hybrid. Public clouds 108 may include public servers that are maintained by third parties to the clients 165 or the owners of the clients 165. The servers may be located off-site in remote geographical locations as disclosed above or otherwise. Public clouds 175 may be connected to the servers over a public network 170. Private clouds 175 may include private servers that are physically maintained by clients 165 or owners of clients 165. Private clouds 175 may be connected to the servers over a private network 170. Hybrid clouds 175 may include both the private and public networks 170 and servers.

The cloud 175 may include back-end platforms, e.g., servers, storage, server farms, or data centers. For example, the cloud 175 can include or correspond to a server or system remote from one or more clients 165 to provide third-party control over a pool of shared services and resources. The computing environment 160 can provide resource pooling to serve multiple users via clients 165 through a multi-tenant environment or multi-tenant model with different physical and virtual resources dynamically assigned and reassigned responsive to different demands within the respective environment. The multi-tenant environment can include a system or architecture that can provide a single instance of the software, an application, or a software application to serve multiple users. Each tenant can include one or more clients. The multi-tenant environment can include user security features (e.g., identify management, single sign-on, etc.). In some embodiments, the computing environment 160 can provide on-demand self-service to unilaterally provision computing capabilities (e.g., server time, network storage) across a network for multiple clients 165. The computing environment 160 can provide elasticity to dynamically scale out or scale in responsive to different demands from one or more clients 165. In some embodiments, the computing environment 160 can include or provide monitoring services to monitor, control, and/or generate reports corresponding to the provided shared services and resources.

In some embodiments, the computing environment 160 can include and provide different types of cloud computing services. For example, the computing environment 160 can include Infrastructure as a Service (IaaS). The computing environment 160 can include Platform as a Service (PaaS). The computing environment 160 can include server-less computing. The computing environment 160 can include Software as a Service (SaaS). For example, the cloud 175 may also include a cloud-based delivery, e.g., Software as a Service (SaaS) 180, Platform as a Service (PaaS) 185, and Infrastructure as a Service (IaaS) 190. IaaS may refer to a user renting the use of infrastructure resources that are needed during a specified time period. IaaS providers may offer storage, networking, servers, or virtualization resources from large pools, allowing the users to quickly scale up by accessing more resources as needed. Examples of IaaS include AMAZON WEB SERVICES provided by Amazon.com, Inc., of Seattle, Washington; RACKSPACE CLOUD provided by Rackspace US, Inc., of San Antonio, Texas; Google Compute Engine provided by Google Inc. of Mountain View, California; or RIGHTSCALE provided by RightScale, Inc., of Santa Barbara, California. PaaS providers may offer functionality provided by IaaS, including, e.g., storage, networking, servers, or virtualization, as well as additional resources such as, e.g., the operating system, middleware, or runtime resources. Examples of PaaS include WINDOWS AZURE provided by Microsoft Corporation of Redmond, Washington; Google App Engine provided by Google Inc.; and HEROKU provided by Heroku, Inc., of San Francisco, California. SaaS providers may offer the resources that PaaS provides, including storage, networking, servers, virtualization, operating system, middleware, or runtime resources. In some embodiments, SaaS providers may offer additional resources including, e.g., data and application resources. Examples of SaaS include GOOGLE APPS provided by Google Inc.; SALESFORCE provided by Salesforce.com Inc. of San Francisco, California; or OFFICE 365 provided by Microsoft Corporation. Examples of SaaS may also include data storage providers, e.g., DROPBOX provided by Dropbox, Inc., of San Francisco, California; Microsoft SKYDRIVE provided by Microsoft Corporation; Google Drive provided by Google Inc.; or Apple ICLOUD provided by Apple Inc. of Cupertino, California.

Clients 165 may access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards may allow clients access to resources over HTTP and may use Representational State Transfer (REST) protocol or Simple Object Access Protocol (SOAP). Clients 165 may access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that may be built on REST, HTTP, XML, or other protocols. Clients 165 may access SaaS resources through the use of web-based user interfaces, provided by a web browser (e.g., GOOGLE CHROME, Microsoft INTERNET EXPLORER, or Mozilla Firefox provided by Mozilla Foundation of Mountain View, California). Clients 165 may also access SaaS resources through smartphone or tablet applications, including, e.g., Salesforce Sales Cloud or Google Drive app. Clients 165 may also access SaaS resources through the client operating system, including, e.g., Windows file system for DROPBOX.

In some embodiments, access to IaaS, PaaS, or SaaS resources may be authenticated. For example, a server or authentication server may authenticate a user via security certificates, HTTPS, or API keys. API keys may include various encryption standards such as e.g., Advanced Encryption Standard (AES). Data resources may be sent over Transport Layer Security (TLS) or Secure Sockets Layer (SSL).

Figure 2:
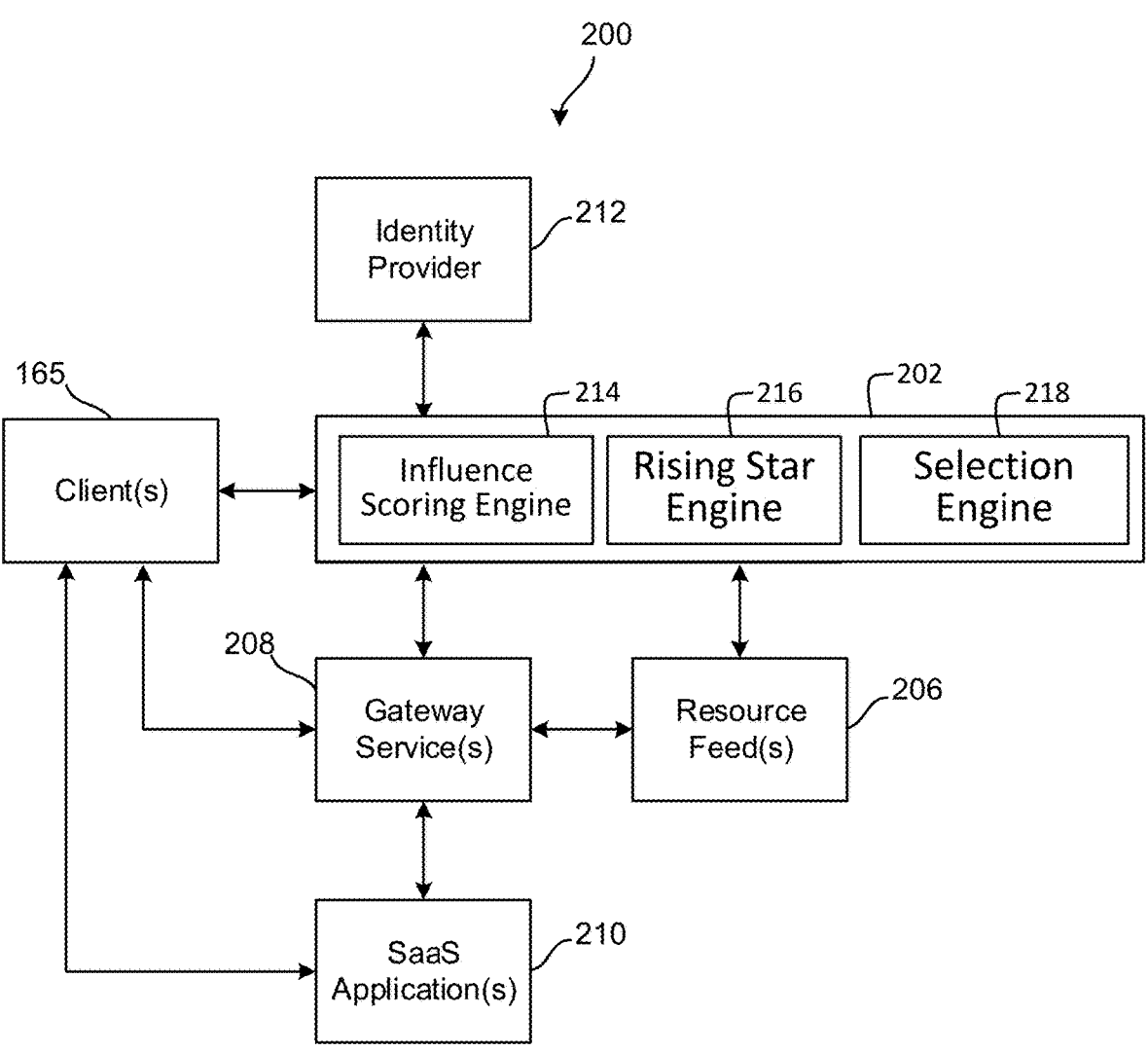
FIG. 2 is a block diagram of an example system in which profile filtering management services may manage and streamline access by clients to resource feeds (via one or more gateway services) and/or software-as-a-service (SaaS) applications.

FIG. 2 is a block diagram of an example system 200 in which a profile filtering engine 202 may generate an interactive electronic platform on a user interface and transmit the user interface to the clients 165. Users of the clients 165 may access the interactive electronic platform and submit requests for a list of influential medical entities and medical entities that are projected to be influential in the future. The profile filtering engine 202 may receive the request and receive data from resource feeds 206 that provide clinical data and/or online interaction data regarding different medical entities. The profile filtering engine 202 may feed the clinical data and/or online interaction data through an influence scoring engine 214 (e.g., one or more machine learning models) to generate influence scores for individual medical entities. After obtaining the influence scores, the profile filtering engine 202 may feed clinical data and/or online interaction data of a subset of medical entities through a rising star engine 216 (e.g., one or more machine learning models) to generate predicted influence scores for the subset of medical entities. The selection engine 218 may identify the current and predicted influence scores and select the profiles with the highest current influence scores as key opinion leaders and the profiles that are predicted to have the highest influence scores as rising stars. The profile filtering engine 202 may generate a record comprising identifications of the key opinion leaders and rising stars that may be viewed on a graphical user interface to illustrate the most influential medical entities.

As described herein, Key Opinion Leaders may be the most influential medical entities that the profile filtering engine 202 identifies through its filtering process. Although many different factors may be used to identify key opinion leaders, examples of medical entities the profile filtering engine 202 may identify through the filtering process include, but are not limited to, medical entities with high patient referrals, an extensive referral network, a high social media voice, held leadership positions, a large number of publications, high clinical trial participation, and activity in conferences as speakers. Similarly, rising stars may be individuals that the profile filtering engine 202 identifies as not having the same influence as key opinion leaders at the time the data is processed, but that are predicted to be key opinion leaders with similar qualities in the future.

In one example, the profile filtering engine 202 may employ an identity provider 212 to authenticate the identity of a user of a client 165 and, following authentication, grant the user access to the interactive electronic platform. Via the accessed client 165, the user may input a request for key opinion leaders and/or rising stars. The profile filtering engine 202 may receive the input and execute a series of models (e.g., machine learning models and optimization models) in the influence scoring engine 214, the rising star engine 216, and the selection engine 218. In some implementations, the client 165 may communicate with the profile filtering engine 202 via gateway services 208. In some implementations, the client 165 may access the profile filtering engine 202 directly through SaaS application(s) 210. The SaaS application(s) 210 may allow the client 165 to access the electronic platform discussed herein and view data that was collected from the resource feeds 206.

The client(s) 165 may be any type of computing device capable of accessing the resource feeds 206 and/or the SaaS applications 210, and may, for example, include a variety of desktop or laptop computers, smartphones, tablets, etc. Each of the profile filtering engine 202, the resource feeds 206, the gateway services 208, the SaaS applications 210, and the identity provider 212 may be located within an on-premises data center of an organization for which the system 200 is deployed, within one or more cloud computing environments, or elsewhere.

Section B: Profile Filtering System

Figure 3:
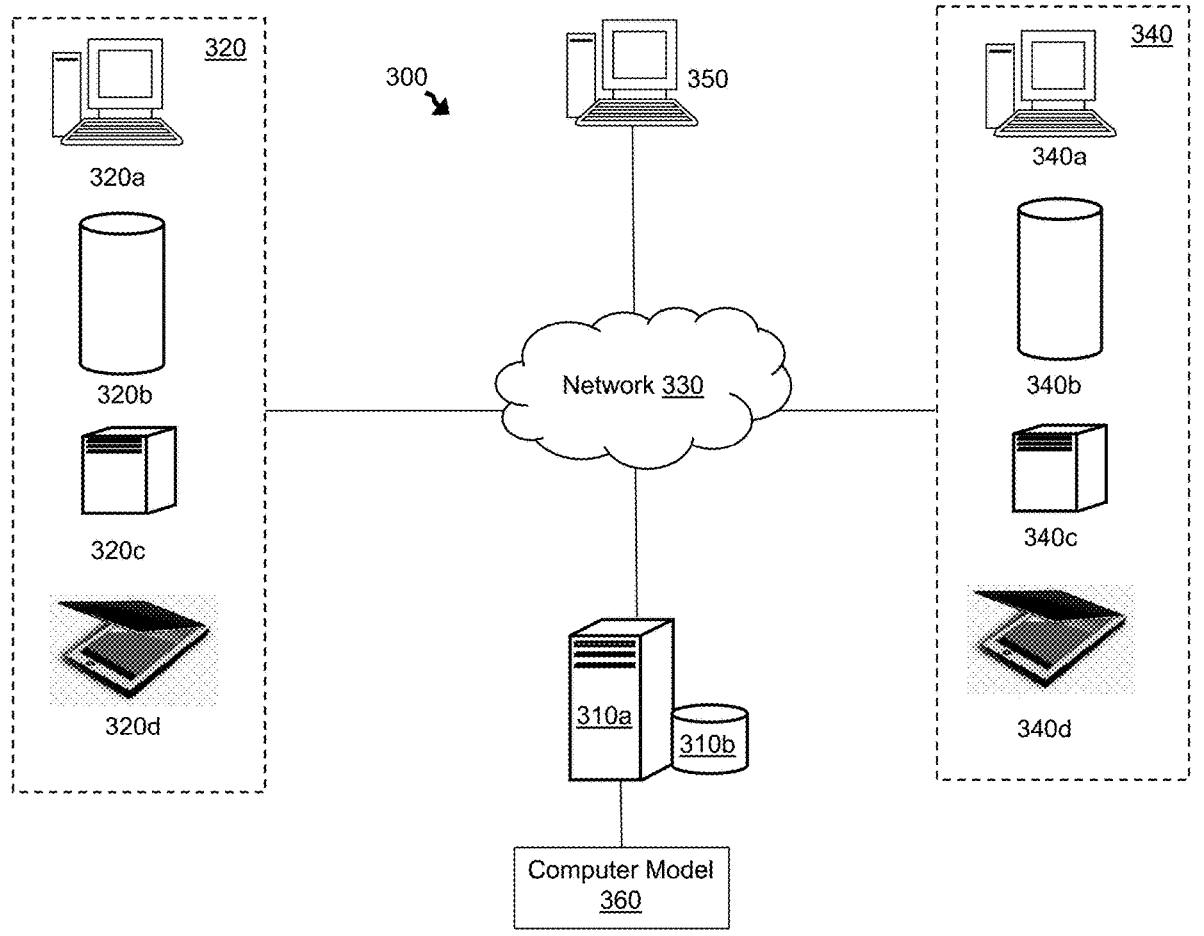
FIG. 3 is an example computing environment for implementing a multi-model architecture for filtering entity profiles, in accordance with one or more implementations.

As will be described throughout, a server of a profile filtering system 300 (such as an analytics server 310*a*) can retrieve and analyze data using various methods described herein to select key opinion leaders and/or rising stars using a series of models (e.g., machine learning models and/or optimization models). In doing so, the server may optimize company resources to select the most influential individuals to interact with others online. FIG. 3 is a non-limiting example of components of the profile filtering system 300 in which the analytics server 310*a* operates. The analytics server 310*a* may be any computer, server, or processor.

The analytics server 310*a* may utilize components described in FIG. 3 to retrieve data and to generate/display results. The analytics server 310*a* may be communicatively coupled to a system database 310*b*, electronic data sources 320*a-d* (collectively electronic data sources 320), end-user devices 340*a-d* (collectively end-user devices 340), and/or an administrator computing device 350. The system 300 is not confined to the components described herein and may include additional or alternative components, not shown for brevity, which is to be considered within the scope of the embodiments described herein.

The above-mentioned components may be connected through a network 330. The examples of the network 330 may include, but are not limited to, private or public LAN, WLAN, MAN, WAN, and the Internet. The network 330 may include both wired and wireless communications according to one or more standards and/or via one or more transport mediums.

The analytics server 310*a* may utilize one or more application programming interfaces (APIs) to communicate with one or more of the electronic devices described herein. For instance, the analytics server may utilize application programming interfaces (APIs) to automatically receive data from the electronic data sources 320. The analytics server 310*a* can receive data as it is generated, monitored, and/or processed by the respective electronic data source 320. For instance, the analytics server 110*a* may utilize an API to receive clinical data and/or online interaction data from the database 320*b* without any human intervention. This automatic communication allows for faster retrieval and processing of data.

As described herein, clinical data is data that is descriptive or otherwise associated with a medical field, a medical topic, a medical professional (e.g., a doctor, nurse, or social worker), and/or a healthcare provider. Examples of clinical data include, but are not limited to competitive engagement data, data from congress, clinical trial data, publication data, real-world data, channel affinity data, speaker bureau customer master affiliation data and engagement data, etc. Clinical data can also include industry engagement, and leadership engagement data. The clinical data may be associated with medical entities if the medical entities were involved in generating the clinical data (e.g., the medical entity authored or co-authored a publication, the medical entity performed a clinical trial and uploaded the data for the clinical trial, etc.). In some implementations, to establish the association between an entity and clinical data, the analytics server may receive the clinical data and scan (e.g., using optical character recognition (OCR) techniques and/or a fuzzy matching algorithm (e.g., an edit distance formula)) the clinical data to determine if there is a string that matches a medical entity's name. If there is a match, the data processing system may label the data or an entity profile associated with the medical entity to indicate the clinical data is associated with the medical entity.

Similarly, as described herein, online interaction data may be any actions that a medical entity takes on a web-based property (e.g., a website, a web page, a social media page such as a personal profile, a user account page, etc.), such as posting a blog post, commenting on an article or a picture, liking an article or an image, viewing a video including the amount of time the user viewed the video, direct messages, relationships (e.g., connections or friendships), etc. Online interaction data may also include data about a user's online profile, such as friends, connections, other types of relationships between the profile and other online profiles. In some implementations, online interaction data may be clinical data.

The analytics server 310*a* may generate and/or host an electronic platform having a series of graphical user interfaces (GUIs) configured to use various computer models to project and display data associated with selected key opinion leaders and/or rising stars. The electronic platform can be displayed on the electronic data sources 320, the administrator computing device 350, and/or end-user devices 340. An example of the electronic platform generated and/or hosted by the analytics server 310a may be a web-based application or a website configured to be displayed on different electronic devices, such as mobile devices, tablets, personal computers, and the like. Even though certain embodiments discuss the analytics server 310a displaying the results, it is expressly understood that the analytics server 310a may either directly generate and display the electronic platform described herein or may present the data to be presented on a GUI displayed on the end-user devices 340.

The analytics server 310a may host a website (also referred to herein as the electronic platform) accessible to users operating any of the electronic devices described herein (e.g., end-users). In some implementations, the content presented via the various web pages may be controlled based on each particular user's role or viewing permissions. The analytics server 310a may be any computing device comprising a processor and non-transitory machine-readable storage capable of executing the various tasks and processes described herein. Non-limiting examples of such computing devices may include servers, computers, workstation computers, personal computers, and the like. While this example of the system 300 includes a single analytics server 310a, in some configurations, the analytics server 310a may include any number of computing devices operating in a distributed computing environment.

The analytics server 310a may execute one or more software applications configured to display the electronic platform (e.g., host a website), which may generate and serve various web pages to each electronic data source 320 and/or end-user devices 340. Different end-users may use the website to view and/or interact with the predicted results.

The analytics server 310a may be configured to require user authentication based on a set of user authorization credentials (e.g., username, password, biometrics, cryptographic certificate, and the like). In such implementations, the analytics server 310a may access the system database 310b configured to store user credentials, which the analytics server 310a may be configured to reference to determine whether a set of entered credentials (purportedly authenticating the user) match an appropriate set of credentials that identify and authenticate the user.

The analytics server 310a may also store data associated with each user operating one or more electronic data sources 320 and/or end-user devices 340. The analytics server 310a may use the data to determine whether a user device is authorized to view results generated by the computer model(s) discussed herein, such as a computer model 360.

The computer model 360 may be any collection of one or more algorithms and/or machine-readable code that can ingest clinical data and/or online interaction data associated with a medical entity to generate influence scores and/or predicted influence scores for entity profiles. The computer model 360 may include a mathematical algorithm, an optimization or a statistical ranking algorithm (e.g., Technique for Order of Preference by Similarity to Ideal Solution (TOPSIS) such as Multi-Criteria Decision Making (MCDM) TOPSIS) an artificial intelligence or machine learning model (e.g., neural network, a long short term memory neural network, boosting, bagging machine learning, transformer models, etc.) that can be trained in accordance with data received from the electronic data sources 320 and/or end-user devices 340. In some implementations, the analytics server 310 may use the data collected from the electronic data sources 320 to generate a training dataset and further train the computer model 360 using various machine learning training techniques (e.g., supervised, unsupervised, or semi-supervised training).

The analytics server 310a may receive or retrieve clinical data and/or online interaction data from end-user devices 340 and/or electronic data sources 320. The electronic data sources 320 may represent different databases or third-party vendors who possess medical data, marketing data, clinical trial data, online interaction data, and the like. For instance, the electronic data sources 320 may represent computers, databases, and servers of a medical provider that can provide additional information regarding a clinical trial. In some implementations, the analytics server 310a may scrape social media websites (which may be hosted by electronic data sources 320) to retrieve data from the websites such as connection data (e.g., data indicating the medical entities are connected with each other through the websites), comments, blog posts, likes, and/or any other type of online interaction data.

The analytics server 310a may use the data collected from the electronic data sources 320 and received from the end-user device 340 to execute the computer model 360. The analytics server 310a then displays the results via the electronic platform (e.g., GUIs) on the administrator computing device 350 or the end-user devices 340.

The end-user devices 340 may be any computing device comprising a processor and a non-transitory machine-readable storage medium capable of performing the various tasks and processes described herein. Non-limiting examples of an end-user device may include workstation computers, laptop computers, tablet computers, and server computers. In operation, various end-users may use end-user devices 340 to access the electronic platform operationally managed by the analytics server 310a to request and view key opinion leaders and/or rising stars, as predicted by the analytics server 310a using the model 360.

The administrator computing device 350 may represent a computing device operated by a system administrator. The administrator computing device 350 may be configured to display retrieved data, in the form of results generated by the analytics server 110a, where the system administrator can monitor various models utilized by the analytics server 110a, review feedback, and modify various thresholds/rules described herein.

The analytics server 310a may access, generate, and execute various computer models. Although the example system 300 depicts the computer model 360 stored on the analytics server 310a, the model 360 may be stored on another device or server (e.g., stored locally or in cloud storage).

In operation, the analytics server 310a may collect various types of clinical data and/or online interaction data about, generated by, or otherwise associated with different medical entities. The analytics server 310a may then train the one or more models of the computer model 360 to develop an algorithm to calculate influence and predicted influence scores for individuals. When the computer model 360 is trained, the analytics server 310 may implement the computer model and allow end-users to use the computer model 360 to view key opinion leaders with the highest influence scores calculated based on the clinical data and/or online interaction data and rising stars that are projected to have high influence scores in the future. For instance, an end-user may use any of the end-user devices 340 to access the electronic platform and request to view key opinion leaders and/or rising stars. The analytics server 310*a* may then execute the computer model 360 to generate influence scores for entity profiles and select key opinion leaders and/or rising stars based on the influence scores. The analytics server 310*a* may generate a record comprising strings identifying the key opinion leaders and the rising stars and populate the electronic platform with the record.

The electronic platform may include various GUIs discussed herein where each GUI may include various input elements allowing the end-user to request to view key opinion leaders and/or rising stars.

Section C: Profile Filtering Method

Referring now to FIG. 4, a flowchart of an example method 400 for implementing a multi-model architecture for filtering entity profiles is shown, in accordance with one or more implementations. The method 400 may be performed by a data processing system (e.g., the profile filtering engine 202, the analytics server 310*a*, a client device 165, or any other computing device). The method 400 may include any number of steps and the steps may be performed in any order. Performance of the method 400 may enable the data processing system to use a series of models to automatically generate and filter entity profiles for medical entities to identify the current most influential medical entities and the medical entities that are predicted to be influential in the future. By performing the method 400, the data processing system may select and generate a list of medical entities that are the most influential and/or that are predicted to be the most influential. The data processing system may do so based on clinical data and online-interaction data. The data processing system may do so without relying on any human guessing or analysis based on a small subset of data, as is often done in conventional systems.

At step 402, the data processing system may receive clinical data and/or online interaction data for a plurality of medical entities. As described herein, medical entities may be or include any medical professional or other type of healthcare provider. The data processing system may receive multiple different types of clinical data and receive the clinical data from different sources. For example, the data processing system may receive online interaction data, competitive engagement data, data from congress, clinical trial data, publication data, real-world data, channel affinity data, speaker bureau customer master affiliation data and engagement data, etc., from various servers or computing devices. In some cases, the different servers or sets of servers may provide different types of data (e.g., one server may provide clinical data, such as medical trial data, while another server may provide online interaction data). In one example, the clinical data may be or include publications authored or co-authored by the individual medical entities. In some implementations, the clinical data and/or online interaction may include text and/or images describing different medical fields such as new procedures, medical inventions, diseases, diagnosis techniques, etc.

The data processing system may receive the clinical data through different methods, depending on the data source. In one example, the data processing system may simply receive clinical data from a data source after the data source transmitted the clinical data to the data processing system. Such may be the case, for example, when the data processing system has a pre-existing relationship (e.g., an established connection) with the data source and the data source is configured to transmit new clinical data to the data processing system upon receipt, upon a defined time interval passing, or upon receipt of a request for the clinical data from the data processing system. In another example, the data processing system may use web scraping techniques to retrieve data from various web pages. To do so, the data processing system may retrieve data from the servers or computers hosting the website after identifying the clinical data and/or online interaction and the medical entities that are associated with (e.g., named in) the clinical data or online interaction data. Such may be the case, for example, when the data processing system retrieves data from social media websites. In some implementations, the data processing system may collect online interaction data and/or clinical data using screen scraping techniques on the websites.

At operation 404, the data processing system may generate entity profiles and a network graph data structure. The data processing system may generate the entity profiles and the network graph data structure from the received clinical data and online interaction data. Entity profiles may be data structures that include medical entities' names, demographic information about the medical entities, and/or any clinical data or online interaction data the data processing system has stored in the respective entity profiles. In some implementations, the data processing system may store pointers to the locations of the clinical data and/or online interaction data in the entity profiles, thus conserving memory resources by avoiding storing duplicative copies of clinical data and/or online interaction data locally when the data can be accessed and retrieved from another host computing device or database. Each profile may include a string identification of the entity that is associated with the profile and/or a unique identifier the data processing system generates (e.g., generates using a pseudo-random number generator). The data processing system may use such identifications to link or insert new clinical data and/or online interaction data into the respective profiles and/or to group the entity profiles together for fast retrieval.

To generate the entity profiles, the data processing system may implement various matching techniques (e.g., exact matching or fuzzy matching) between strings in data files or data packets in the clinical data and/or online interaction data and strings in the individual profiles. For example, the data processing system may identify and/or extract a name of an author from a publication from a particular field the data processing system may be trained to query, or from text the data processing system identified using natural language processing techniques (NLP). The data processing system may identify either exact matches (e.g., matching strings in which each character matches) or fuzzy matches (e.g., matching strings that do not have the exact same characters, but are similar above a defined threshold percentage or number of characters) between the identified strings of names in the clinical data and the different entity profiles. In some implementations, the data processing system may identify fuzzy matches based on a comparison between the strings and/or using an edit distance algorithm. Upon identifying a match between a file or data packet of clinical data and an entity profile, the data processing system may store the file or data packet in the matching entity profile.

In some cases, the data processing system may identify a name in the clinical data or online interaction data that does not match names in any profiles of the network data structure. When this occurs, the data processing system may "enrich" the network data structure and generate a new data structure for a new profile containing the name. After generating the new profile, the data processing system may perform the same updating steps as listed above to update the profile with clinical data associated with the name.

The data processing system may generate the network graph data structure with the entity profiles. To do so, the data processing system may generate edges or connections between entity profiles that are connected or have a relationship in some manner. For example, when the data processing system identifies a data file or a data packet with multiple names (e.g., a publication with co-authors), the data processing system may identify the entity profiles that match each name. Additionally, because the data processing system identified the names from the same data file or data packet, the data processing system may determine the entity profiles have at least some sort of relationship with each other. Accordingly, the data processing system may generate an edge or connection between the two entity profiles. In another example, the data processing system may determine entity profiles have connections responsive to identifying posts by one medical entity on a social media page of another medical entity. The post may indicate the two medical entities are related, and therefore cause the data processing system to generate an edge between the two profiles. In yet another example, the data processing system may generate an edge between two entity profiles that participated in a clinical experiment together. In yet another example, the data processing system may generate edges between entity profiles for working at the same company (e.g., in the same hospital), in which case the data processing system may determine the entities work at the same company by analyzing a human resources form or scraping a company web page indicating the company's employees. In yet another example, the data processing system may identify a common patient name from healthcare forms of two different medical entities and generate an edge between the medical entities based on the identification. The data processing system may generate edges between entity profiles for any similar reasons.

In some implementations, to generate the edges between entity profiles, the data processing system may insert pointers into both entity profiles. The pointers may point to the other entity profile connected to the edge. The pointers may be selectable addresses to quickly access data of the other entity profile or otherwise an identification of the other entity profile to indicate there is an edge between the two entity profiles.

In some implementations, in addition to the pointers, the data processing system may calculate a distance score for each of the edges. The data processing system may calculate the distance score as a function of the affinity score of the connection and/or whether the connection is direct. The affinity score may indicate a degree of closeness of the relationship. The data processing system may calculate the affinity score using a set of affinity rules that indicate the basis on which to evaluate the affinity of individual connections between medical entities. For example, the set of affinity rules may include a rule that indicates being employed by the same company would result in a high affinity score. In another example, the set of affinity rules may include a rule indicating graduating from the same school would result in a low affinity score unless there is another connection or relationship between the two medical entities (e.g., the two graduated from the same school then went on to work at the same company). In yet another example, the set of affinity rules may include indicating sharing a patient results in a high closeness. In some implementations, the data processing system may use such rules in combination with Dijkstra's algorithm to calculate the affinity score. The set of affinity rules may include any number and/or type of such rules.

In some implementations, the data processing system may determine the degree of connection as being a direct or a second degree connection. To do so, the data processing system may identify how the connection was created (e.g., the type of data file or data packet that resulted in the generation of the connection) and determine whether the connection is a direct connection or not according to a set of connection rules (e.g., a connection resulting from working for that same employer may be a second degree connection while a connection resulting from a message between the two entities may be a direct connection). In one example, the data processing system may determine whether a connection is direct by determining if the entities associated with the entity profiles have communicated directly with each other (e.g., have transmitted messages to each other, have co-authored a publication together, etc.) or have been associated with a common event, building, or individual.

Upon determining the affinity score of a connection and whether the connection is a direct connection or a second degree connection, the data processing system may calculate a distance score for the connection. The data processing system may calculate the distance score using any function, such as an average, a sum, a weighted average, a weighted sum, a multiplier (e.g., a direct connection may be associated with one value and a second degree connection may be associated with another value; the value may be multiplied by the corresponding closeness score to obtain the affinity score), etc. Any function may be used to calculate the distance score for the connection.

The data processing system may store one or more of the type of the degree of connection, the distance score of the connection, or the affinity score of the connection in one or both of the connected profiles. In this way, the data processing system may later retrieve the stored data to insert into a machine learning model, an optimization algorithm, and/or graph-based models (which may be used to link network data) to select key opinion leaders and/or rising stars to present the stored data to a user on a user interface. In some implementations, the data processing system may retrieve such data as raw data to present to a user to illustrate the cause for the selections.

At operation 406, the data processing system may calculate clinical metrics and online interaction metrics for the entity profiles. The data processing system may calculate the clinical metrics and online interaction metrics and/or separately evaluate different types of clinical data and/or online interaction data. For instance, in some implementations, the data processing system may maintain one or more counters for each of the different types of clinical data. The counts of the counters may be clinical metrics. In one example, the data processing system may maintain and increment a counter for an individual for each publication the individual authored or co-authored. Each instance in which the data processing system identifies the individual's name as an author of a different publication, the data processing system may increment the counter. In another example, the data processing system may maintain a counter for the number of posts an individual has made on a single or multiple social media sites (e.g., maintain a separate counter for each social media site or a single counter for all social media sites with which the individual has interacted). The data processing system may scrape the data from the social media sites and increment the counter for each post the individual made on the sites. In another example, the data processing system may maintain and/or increment a counter for each connection a user has in the network graph data structure. The data processing system may maintain and increment such counters for any number of types of clinical data. Clinical metrics can also include scientific metrics, patient management metrics, industry engagement metrics, and leadership engagement metrics. Other examples of counters and metrics for different types of clinical data the data processing system may maintain are below:

1. COMMERCIAL METRICS: total number of patients, therapy adoption speed, total number of treated patients, total diagnosed patient count, total drug patient count, total procedure patient count;
2. PUBLICATION METRICS: number of publications, number of therapy related publications, latest pub title, number of case report publications, number of publications as first author;
3. CLINICAL TRIAL METRICS: number of clinical trials, number of ongoing clinical trials, number of therapy related clinical trials, average identified sites, number of academic sponsored clinical trials, latest clinical trial title, number of clinical trials in the United States, number of industry sponsored clinical trials;
4. CONGRESS ABSTRACT METRICS: number of congress abstracts, number of therapy related congress abstracts, latest congress abstract date;
5. OPEN PAYMENT METRICS: research payment, speaking payment, consulting payment, food and beverage payment, associate research payment, total open payment amount, top brand;
6. CONNECTION METRICS: number of referral connections, number of publication connections, number of clinical trial connections, number of congress connections, number of total connections;
7. DESK RESEARCH METRICS: total number of engagements; and
8. PII METRICS: phase experience, referral patient received count, recent trials completed, biomarker method of analysis experience.

The data processing system may calculate such metrics and, in some implementations, store the metrics in the entity profiles of the medical entities that correspond to the calculated metrics.

In some implementations, the data processing system may additionally calculate online interaction metrics for medical entities. Online interaction metrics may be or include data generated from online interaction data similar to the clinical metrics described above. The data processing system may calculate online interaction metrics using counters and other methods similar to how the data processing system calculated clinical metrics. Examples of online interaction metrics include:

1. SOCIAL MEDIA METRICS: number of followers, number of posts, number of retweeted hcps, last post date, number of shares, twitter verified.

The data processing system may calculate such metrics and, in some implementations, store the metrics in the entity profiles that correspond to the calculated metrics.

In some implementations, the data processing system may store the calculated clinical and online interaction metrics for retrieval. For example, after calculating the clinical and online interaction metrics, the data processing system may store the metrics in the data structures of the entity profiles for which the metrics were calculated or otherwise in memory with an identification of the entity profiles. The data processing system may also label the stored metrics with the type of the metric (e.g., clinical or online interaction metric, a connection metric, a social media metric, a clinical trial metric, etc.). Accordingly, when the data processing system receives a request for a specific type of metric for an entity that was selected to be a rising star or a key opinion leader, the data processing system may quickly identify the metric from the profile and based on the requested type of metric. Such may be advantageous, for example, if a user seeks to learn the reasoning as to why an entity was or was not selected.

At operation 408, the data processing system may execute a model to generate influence scores for the plurality of entity profiles. An influence score may indicate a degree of influence a medical entity may have based on the medical entity's online activity (e.g., the amount of online interaction the medical entity performs) and real-world medical activity (e.g., the amount of publications, clinical trials, and/or other types of data in the medical field the medical entity generates). The data processing system may input the calculated clinical and online interaction metrics with identifications of the entity profiles that correspond to the metrics into the model to calculate such influence scores for the medical entities.

The model may be or include one or more machine learning models and/or optimization models. In one implementation, the data processing system may execute the model by executing a TOPSIS algorithm (e.g., an MCDM TOPSIS algorithm) that is configured to output an influence score for a medical entity based on clinical metrics and/or online interaction metrics calculated for the medical entity. To do so, the data processing system may set weights and impacts for the different clinical metrics and/or online interaction metrics by retrieving the weights and impacts from memory. The data processing system may set or calculate the weights by using a CRITIC method as an objective weighting method. The data processing system may then input the metrics into the TOPSIS algorithm and the TOPSIS algorithm may apply the weights and impacts to the metrics respectively to generate an influence score for the entity profile associated with the medical entity.

In some implementations, the data processing system may generate influence scores for each or a subset of the entity profiles of the network graph data structure. The data processing system may retrieve clinical data from their respective profiles and calculate metrics from the retrieved data. The data processing system may then separately input the calculated metrics into the TOPSIS algorithm to generate influence scores for the medical entities. The data processing system may compare the generated influence scores and generate a ranking list of the medical in ascending or descending order based on the influence scores compared with each other.

In some implementations, the data processing system may retrieve the weights and/or impacts for the TOPSIS algorithm based on the source of a request for key opinion leaders and/or rising stars. For example, different group entities (e.g., companies) may value different types of clinical data or online interaction data differently, and therefore prefer different weights and/or impacts from each other. Upon receiving a request for key opinion leaders and/or rising stars, the data processing system may identify the group entity that is associated with the request from at least one of an identifier of the group entity in the request, the user profile of the individual that submitted the request, or a device identifier (e.g., an IP address of the computing device that submitted the request). The data processing system may identify the group entity and use a look-up technique in memory to identify the weights and/or impacts that are stored in an entity profile data structure for the group entity to use to execute the TOPSIS algorithm In some implementations, the data processing system may use machine learning techniques to identify the proper weights or parameters for the TOPSIS algorithm. For example, the data processing system may execute a machine learning model (e.g., a support vector machine, a neural network, a random forest, etc.) to predict weights and/or impacts for the TOPSIS algorithm. The data processing system may feed training data (e.g., clinical metrics and/or online interaction metrics) into the TOPSIS algorithm and the TOPSIS algorithm may output an influence score based on the training data. A user may submit or provide an input indicating whether the influence score is correct and/or the correct influence score. The data processing system may feed the input back into the machine learning model that calculated the weights and/or impacts for the TOPSIS algorithm for training. The machine learning model may use back-propagation techniques on its own weights and parameters for training for each iteration of training until the machine learning model predicts the proper weights and/or impacts for the TOPSIS algorithm to an accuracy above a defined accuracy threshold. In this way, the data processing system may determine the proper weights for the TOPSIS algorithm to accurately predict speaker scores for medical entities.

In some implementations, upon generating the influence scores and/or the predicted influence scores for entity profiles, the data processing system may store the scores for the entity profiles in the profiles of the respective entity profiles. To do so, the data processing system may insert the influence scores with labels indicating they are influence scores or predicted influence scores in the data structures of the profiles. Accordingly, in response to receiving a request (e.g., a request from a client device) for the scores for one or more of the entity profiles, the data processing system may retrieve the scores from the profiles to send in response to the request.

At operation 410, the data processing system may segment the entity profiles based on their respective influence scores. The data processing system may segment the model by calculating one or more thresholds for the influence scores of the medical entities. The data processing system may do so, for example, by calculating a first threshold that can be used to identify key opinion leaders and a second threshold that can be used to identify rising stars. The data processing system may calculate the first threshold using a formula such as calculating the mean and standard deviation of all of the influence scores and adding a defined number of the calculated standard deviations to the mean. Similarly, the data processing system may calculate the second threshold by adding a defined number of standard deviations to the mean such that the second threshold is smaller than the first threshold. In other examples, the first and second thresholds may be percentiles of the influence scores, predetermined rankings of the influence scores, etc. The data processing system may use any formula to calculate the first and second thresholds.

In some implementations, the data processing system may segment the entity profiles using machine learning techniques. For example, after generating the influence scores for the medical entities, the data processing system may generate a feature vector with the influence scores as values in various indices of the feature vector (e.g., in ascending or descending order within the feature vector). The data processing system may insert the feature vector of influence scores into a machine learning model (e.g., random forest, a support vector machine, a clustering algorithm, a neural network, an XGBoost model, a LightGBM model, etc.). The data processing system may execute the machine learning model using the feature vector as input to generate a first threshold influence score indicating the minimum influence score a medical entity can have to be considered a key performance leader. In some implementations, the machine learning model may also output a second threshold influence scores that indicate a minimum influence score for a medical entity to be considered to be a rising star or a potential rising star. The data processing system may identify the entity profiles and/or medical entities that are associated with influence scores above one or both of the thresholds to filter out any medical entities that are not influential enough to be considered to be a key opinion leader.

In some implementations, the data processing system may train the machine learning model for segmentation using a supervised training method. For example, the data processing system may generate the first and second threshold using internal weights and/or parameters of the machine learning model. The data processing system may output the two thresholds to a user interface. A user or technician viewing the user interface may input an indication of whether one or both of the thresholds are correct and/or the correct thresholds into the user interface. The data processing system may receive the inputs and use back-propagation techniques according to the input values to adjust the weights and/or parameters of the machine learning model for training.

At operation 412, the data processing system may select a subset of entity profiles with influence scores that satisfy a selection criteria. In some implementations, the selection criteria may be a requirement for an influence score to be in a highest segment (e.g., above the first threshold). The data processing system may compare the influence scores to the calculated first and second threshold and identify the influence scores that are above both thresholds (or above the first threshold as the highest threshold). Upon identifying the influence scores that are above both thresholds, the data processing system may identify and select the entity profiles associated with the identified influence scores above the first threshold as the key opinion leaders of the medical entities that were evaluated.

In some implementations, after selecting the subset of entity profiles, the data processing system may refine or filter the selected entity profiles to obtain a final set or list of key opinion leaders. To do so, the data processing system may input the selected list of entity profiles (e.g., the metrics and/or data that was used to calculate the metrics in the profiles) and/or the influence scores of the selected list of entity profiles into a machine learning model, such as XGBoost. The data processing system may execute the machine learning model with the input to generate an updated list of key opinion leaders. In doing so, the data processing system may account for any outliers in the key opinion leaders that may have been improperly selected based on a static segmentation method (e.g., a static formula to calculate the thresholds, such as a percentile or ranking threshold) or based on an influence score that was not adequately calculated or calculated using improperly biased weights. The machine learning model may output the refined list of key performance leaders, which may result in a few of the initially calculated key opinion leaders being removed from the list. The data processing system may output the list to a user interface to illustrate the list to a user accessing a computing device presenting the user interface. In this way, the data processing system may select a refined and accurate list of key opinion leaders.

In some implementations, the data processing system may use a supervised learning technique to train the machine learning model that refines the list of key opinion leaders. For example, the machine learning model may output a refined list of key opinion leaders to a user interface. A user or technician viewing the user interface may provide an input including feedback indicating whether the refined list is accurate or not and/or selections of medical entities that should have remained on or been removed from the list. The data processing system may receive input and adjust the weights or parameters of the machine learning model using back-propagation techniques based on the inputs (e.g., the inputs operate as labels of a set of training data).

In some implementations, the data processing system may select or filter entity profiles based on the entities of the entity profiles being key opinion leaders in a particular geographic area. For instance, the data processing system may identify the connections of the subset of entity profiles that satisfy a selection criteria from the network graph data structure. For each profile, the data processing system may identify the connections that are within a particular defined geographical radius. The data processing system may maintain and increment a geographical influence counter for each profile that has a connection with another medical entity that is located within the defined geographical radius. The data processing system may compare the counts of the geographical influence counters to a threshold and select any entity profiles that have a count exceeding the threshold as key opinion leaders, thus discarding (e.g., removing from memory or from the list of entity profiles) any entity profiles without a count exceeding the threshold.

By filtering entity profiles based on the geographic setting or area in which they are located, the data processing system may identify key opinion leaders that may have more impact in the specified region. In one example, the data processing system may select key opinion leaders in a local setting, such as a community hospital. The data processing system may do so by identifying key opinion leaders that conduct medical activities and have connections within the community hospital. In another example, the data processing system may identify key opinion leaders in a regional setting. The data processing system may do so by identifying key opinion leaders that have connections that are clustered within the region and/or that hold leadership positions in regional chapters of institutions. In yet another example, the data processing system may identify key opinion leaders in a national setting. The data processing system may do so by identifying key opinion leaders that have important roles in research activities (e.g., first author, principal investigator), speak in national congress, and/or hold leadership positions in national institutions, guidelines, patent advocacy groups, etc.

The data processing system may identify key opinion leaders for different geographic settings or areas by calculating metrics for entity profiles from clinical data and/or online interaction data that is associated with the settings (e.g., that was generated within or is otherwise associated with the respective settings) and using the systems and methods described herein to identify the key opinion leaders using the metrics. In some implementations, instead of only using clinical data and/or online interaction data from the specific settings, the data processing system may identify key opinion leaders using all or a subset of the available clinical data or online interaction data and filter out key opinion leaders that do not satisfy specific criteria (e.g., rules) for the individual settings. In some implementations, the data processing system may identify key opinion leaders for the settings by applying rules for the settings directly to the clinical data and/or online interaction data or the clinical metrics and/or online interaction metrics.

In some implementations, the data processing system may select or filter entity profiles based on a key opinion leader type. Key opinion leader types may include scientific key opinion leaders, clinical key opinion leaders, medical/clinical key opinion leaders, principal investigator identifying key opinion leaders, and/or digital key opinion leaders. Scientific focused key opinion leaders may have a high number of publications and citations from other key opinion leaders, a high number of clinical trials in which they participated, and/or active engagement at renowned academy institutions. Clinical key opinion leaders may have a high of therapy related patient population, have acted as an adoption leader or early adopter for therapy, or have extensive referral connections. Digital key opinion leaders may have an active social media presence and/or strong social media followership.

The data processing system may identify key opinion leader types of key opinion leaders based on the clinical metrics and/or online interaction metrics of the key opinion leaders. For example, after identifying key opinion leaders, the data processing system may identify the clinical metrics and/or online interaction metrics that caused the data processing system to identify the key opinion leaders. The data processing system may compare the metrics to rules that correspond to the different key opinion leader types and identify the key opinion leader types for the rules that metrics for the key opinion leaders satisfy. In another example, instead of identifying the types of key opinion leaders for the already selected key opinion leaders, the data processing system may initially select key opinion leaders based on clinical data and/or online interaction data that is associated with the different types. For example, the data processing system may identify data that corresponds to the different key opinion leader types. The data processing system may do so by identifying the sources of the data (which may be associated with specific types of data) or the content of the data using natural language processing techniques. The data processing system may retrieve such data and apply rules to the data or metrics calculated from the data to identify key opinion leaders of the specific types.

In some implementations, the data processing system may insert identifications of key opinion leader, key opinion leader type, and/or key opinion leader setting or area into entity profiles of such labels. For instance, after identifying key opinion leaders, key opinion leader types, and/or key opinion leader region or setting using the systems and methods described herein, the data processing system may generate and insert strings into the profiles associated with the corresponding medical entities. Accordingly, upon later receiving a request for data about individual profiles or for profiles that have such labels, the data processing system may quickly retrieve the strings and/or corresponding profiles to present on the requesting computing device.

At operation 414, the data processing system may identify a second subset of entity profiles based on the influence scores of the second subset. The identified entity profiles of the second subset of entity profiles may be potential rising stars. The data processing system may identify the second subset responsive to each entity profile in the second subset having a score below the first threshold and above the second threshold (e.g., below the highest threshold and above the second highest threshold). The data processing system may compare the influence score of the entity profiles that were not selected in the initial list of key opinion leaders to the first and second thresholds and identify the entity profiles with influence scores that are below the first threshold but above the second threshold. In some implementations, the data processing system may also identify the entity profiles that were removed from the initial list of key opinion leaders during the refinement process described above.

At operation 416, the data processing system may select a third subset of entity profiles as rising stars from the list of potential rising stars identified as described above. To do so, the data processing system may select entity profiles that are projected to be key opinion leaders in the future. For example, in some implementations, the data processing system may identify the age or graduation year from secondary school (e.g., high school, undergraduate school, graduate school, the year the entity obtained a Ph.D. or a post-doctoral degree, etc.) of the potential rising stars from their respective entity profiles. From the identified age or graduation year, the data processing system may filter out any potential rising stars with ages or graduation years that are not within a defined threshold of the current year or date (e.g., filter out entities that have ages above a threshold or who graduated a year too long ago above a threshold (e.g., graduated more than 30 years ago)). In this way, the data processing system may identify potential rising stars that are young and/or are still likely to increase their influence as opposed to any potential rising stars that are more settled and are therefore less likely to continue to increase their influence.

The data processing system may then collect and/or aggregate the clinical and/or online interaction data of the remaining potential rising stars. To do so, the data processing system may identify any clinical and/or online interaction data that is associated with a time stamp within a defined time period of the current time (e.g., data with time stamps from the last five years). In some implementations, the data processing system may do so by selecting pointers in the entity profiles of the potential rising stars to collect the data within the time period. The data processing system may segment the data into individual time frames of the time period (e.g., individual months of the five year period). The data processing system may then calculate clinical metrics and/or online interaction metrics for each of the time frames using methods similar to those described above.

After calculating the clinical metrics and the online interaction metrics for each of the time frames, the data processing system may execute a time series-based forecast algorithm to predict future metrics for the remaining potential rising stars. The data processing system may do so using a machine learning model, such as a long short-term memory (LSTM) model. For example, the data processing system may generate a feature vector with the metrics calculated for each month. The data processing system may input the feature vector into an LSTM model that has been trained to calculate clinical and online interaction metrics for the future based on such feature vectors containing time series metrics. The data processing system may execute the LSTM model using metrics for the remaining potential rising stars to obtain predicted metrics for the remaining potential rising stars.

The data processing system may calculate influence scores for the remaining potential rising stars based on the predicted metrics. To do so, in some implementations, the data processing system may input the predicted metrics into a TOPSIS algorithm (e.g., an MCDM TOPSIS algorithm) such as the TOPSIS algorithm the data processing system used to initially calculate the influence scores for entity profiles. The data processing system may execute the TOPSIS algorithm to obtain predicted influence scores for the remaining potential rising stars.

The data processing system may select the rising stars from the potential rising stars by determining whether the predicted influence scores satisfy a selection criteria. For example, the selection criteria may be or include the first threshold or the second threshold the data processing system previously calculated for the entity profiles. The data processing system may compare the predicted influence scores to the first threshold or the second threshold and determine if the predicted influence scores exceed the respective threshold. If the data processing system determines the predicted influence scores exceed the first or second threshold for any of the potential rising stars, the data processing system may identify and/or select the potential rising stars with such predicted influence scores as a third subset of entity profiles and as rising stars.

In some implementations, upon generating the influence scores and/or the predicted influence scores for entity profiles, the data processing system may store the scores for the entity profiles in the profiles of the respective entity profiles. To do so, the data processing system may insert the influence scores with labels indicating they are influence scores or predicted influence scores in the data structures of the profiles. Accordingly, in response to receiving a request (e.g., a request from a client device) for scores for one or more of the entity profiles, the data processing system may retrieve the scores from the profiles to send in response to the request.

At operation 418, the data processing system may generate a record (e.g., a file, document, table, listing, message, notification, a user interface, an update to a user interface, etc.) comprising identifications of the subsets of the plurality of entity profiles (e.g., the profiles of the key opinion leaders and/or the rising stars). The record may include strings identifying each of the rising stars and the key opinion leaders and, in some cases, string labels indicating which key opinion leaders are associated with which label. The data processing system may store the generated record in memory or in a database for later retrieval. In some implementations, the data processing system may transmit the record to a client device to be displayed on a user interface (e.g., update the user interface with the record). By doing so, the data processing system may inform a user of the selected or identified key opinion leaders and/or rising stars.

In one example embodiment, the data processing system may receive a request for key opinion leaders and rising stars from a computing device. In some cases, the request may include an identification of a geographical setting and/or key opinion leader type. Upon receipt of the request, the data processing system may perform the systems and methods described herein to identify key opinion leaders and rising stars according to the requirements of the request and transmit the identified key opinion leaders and rising stars to the requesting device.

In some implementations, the data processing system may use natural language processing techniques to extract topics and conduct sentiment analysis on clinical data and/or online interaction data. The data processing system may do so to understand what opinion leaders are talking about and their emotions towards those topics and/or medical entities. For example, after identifying key opinion leaders using the systems and methods described herein and presenting them on a computing device, the data processing system may receive a request for a subset of the key opinion leaders that are talking about a particular topic or product. Upon receipt of the request, the data processing system may use natural language processing techniques on the clinical data and/or online interaction data to identify the topics and associated sentiments with which the key opinion leaders are associated. The data processing system may identify any key opinion leaders that were identified as being associated with a matching topic and/or sentiment and transmit identifications of the identified key opinion leaders to the requesting device.

The natural language processing techniques described above may include topic extraction, sentiment analysis, and insights generation. In some cases, the data processing system may perform natural language processing techniques on clinical data and/or online interaction data to generate insights for all medical entities. In topic extraction, the data processing system may segment the text in the data to process shorter text and cluster posts into multiple topic groups. Such topic groups may be tagged such that similar groups may be tagged with the same tags in the future. In sentiment analysis, a machine learning model may ingest the data to perform sentiment analysis. The sentiment analysis may involve considering the emotions the key opinion leaders have towards certain organizations and/or products. In insights generation, the data processing system may identify a trending topic summary (e.g., what are the popular topics discussed by medical entities on social media platforms), a sentiment preference (e.g., what is the feeling/emotion of the medical entities when they post about certain topics), and/or topic preferences (e.g., which topic is the medical entity's preference). By performing natural language processing techniques in this manner, the data processing system may determine what medical entities are posting and discussing, topics and sentiments about those topics, and/or how the topics on social media are changing over time.

Figure 5:
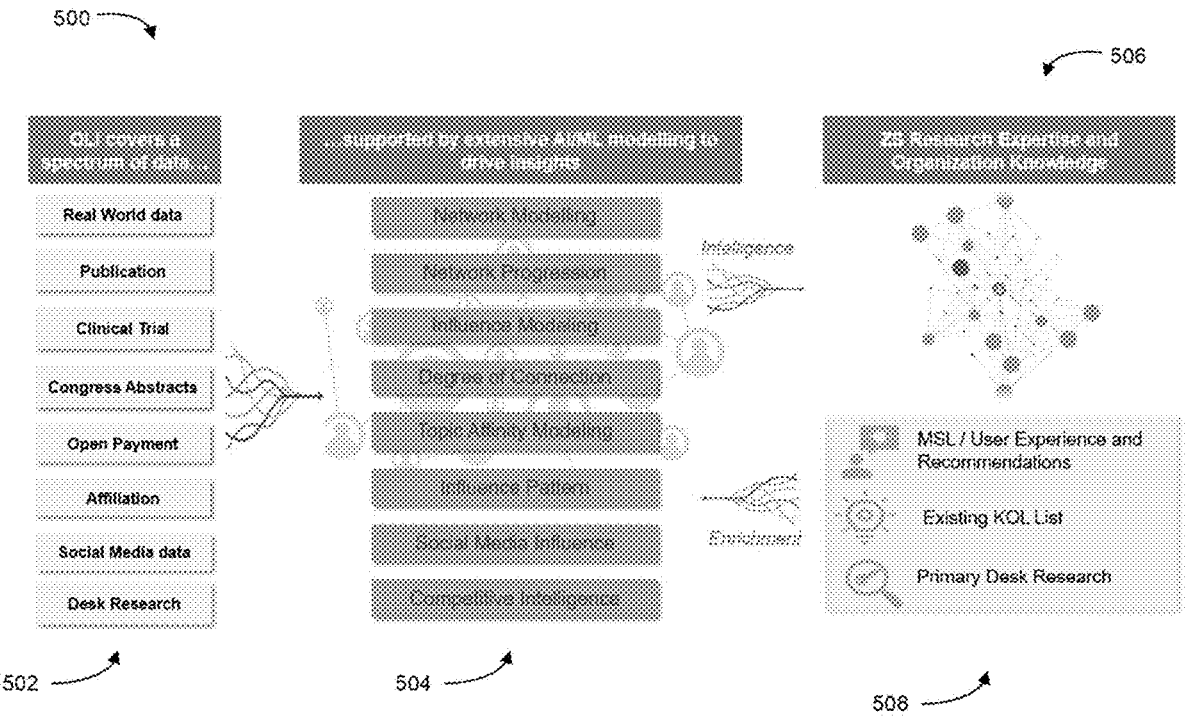
FIG. 5 illustrates a sequence for implementing a multi-model architecture for filtering entity profiles, in accordance with one or more implementations.

Referring now to FIG. 5, an example sequence 500 of implementing a multi-model architecture for filtering entity profiles is shown, in accordance with one or more implementations. The sequence 500 may be performed by a data processing system (e.g., the profile filtering engine 202, the analytics server 310a, a client device 165, or any other computing device). The sequence 500 may include any number of steps and the steps may be performed in any order. In some implementations, performance of the sequence 500 may enable the data processing system to filter out influential medical entities from a vast web of medical entities using online interaction data and clinical data.

At operation 502, the data processing system can gather (e.g., receive and/or retrieve) clinical data and/or online interaction data from a variety of data sources. The data processing system may gather the clinical data using one or more application programming interfaces that enable the data processing system to connect and/or communicate with the computers of the data sources over a network.

At operation 504, the data processing system can generate a network graph data structure and entity profiles for medical entities and calculate influence scores for the entity profiles. The data processing system may generate the network graph data structure using the clinical data and/or the online interaction data the data processing system gathered. The data processing system may calculate the influence scores by calculating metrics for different types of clinical data and/or online interaction data and executing a model with the metrics. The model may include optimization and/or machine learning models or algorithms trained to generate influence scores and predicted influence scores for entity profiles. The data processing system may identify or select key opinion leaders and rising stars based on the influence scores and predicted influence scores. At operation 506, the data processing system may transmit the influence scores, predicted influence scores, rising stars, and/or key opinion leaders to a device that requested such data. In some cases, the data processing system may additionally or instead transmit data indicating how the requested scores or key opinion leaders or rising stars were selected in response to a request or the data that was used to make such selections.

In some embodiments, the data processing system can generate a referral network graph. The referral network graph can include (e.g., illustrate) a patient referral flow between medical entities. The referral network graph can include entity profiles for medical entities that share patient referrals between one another. Via the referral network graph, a user can see how many patients were referred by individual medical entities, the types of the referrals (e.g., treatment procedure, diagnostic procedure, or drug treatment) and/or the direction of the referrals. The direction of the referrals may be indicated in the referral graph by arrows indicating the medical entities to which the patients were referred. For example, the referral network graph can illustrate a number of patients a first medical entity refers to a second medical entity. The referral network graph can illustrate the number of patients the first medical entity refers to the second medical entity for the different types of referrals (e.g., 10 referrals for diagnostic procedure, seven referrals for treatment procedure, nine referrals for drug treatment, etc.). The entity profiles may be linked in the referral network graph by indicators or pointers in the entity profiles of the referral network graph to the different entity profiles associated with the medical entities to which the medical entities refer patients. The links may be separate data structures (e.g., tables) that include the data for the referrals in separate columns (e.g., a row for each referral type and a column for the number of referrals for the respective referral types).

At operation 508, the data processing system may add any data the data processing system generated to the clinical data and/or online interaction data that the data processing system added to the entity profiles in the network graph data structure. The data processing system may identify the data and insert the data into the entity profiles that are associated with the respective pieces of data. For example, the data processing system may insert indications that entity profiles were identified as key opinion leaders and/or rising stars in their respective profiles. In some implementations, the data processing system may insert any scores that the data processing system generated into the respective profiles. By doing so, the data processing system may later use the data to train machine learning models or to transmit to a user whom requests such data.

Figure 6:
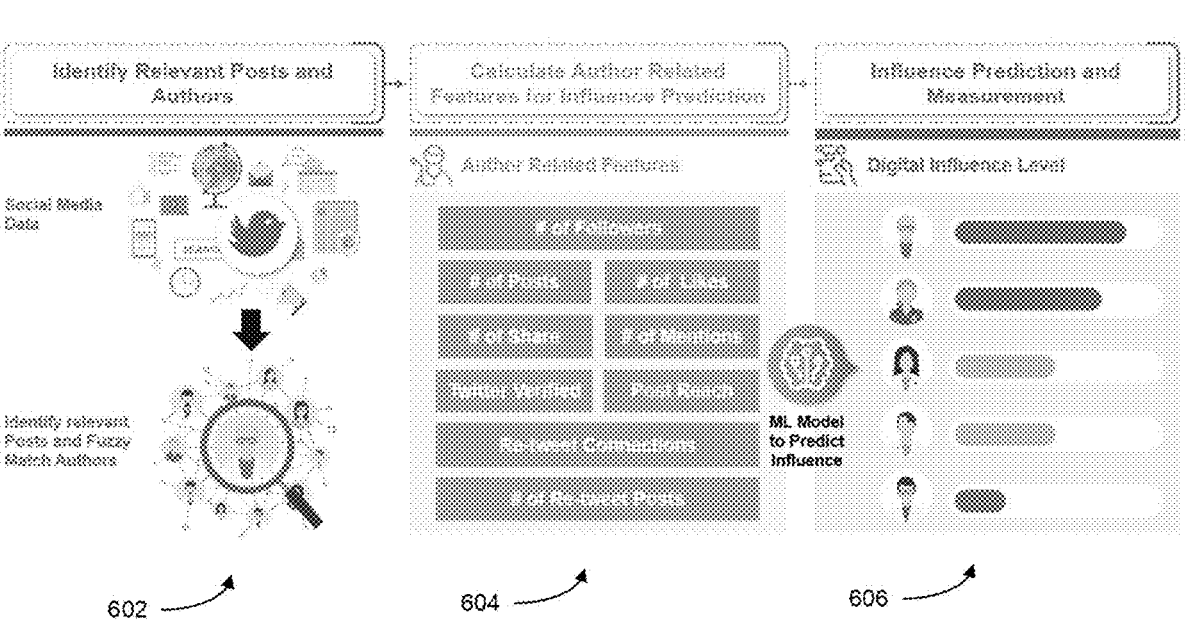
FIG. 6 illustrates another sequence for implementing a multi-model architecture for filtering entity profiles for digital influencer profiling, in accordance with one or more implementations.

Referring now to FIG. 6, another example sequence 600 of implementing a multi-model architecture for filtering entity profiles for digital influencer profiling is shown, in accordance with one or more implementations. The sequence 600 may be performed by a data processing system (e.g., the profile filtering engine 202, the analytics server 310a, a client device 165, or any other computing device). The sequence 600 may include any number of steps and the steps may be performed in any order. In some implementations, performance of the sequence 600 may enable the data processing system to generate influence scores for entity profiles based on online interaction data.

At operation 602, the data processing system may retrieve online interaction data and identify entity profiles of medical entities that are associated with the online interaction data. For example, the data processing system may retrieve the online interaction data by retrieving or receiving the data from servers that host online websites that enable interaction or inputs by their viewers (e.g., social media websites). From the online interaction data, the data processing system may filter through relevant posts (e.g., messages, blog posts, posts, etc.) by authors (e.g., medical entities) using natural language processing techniques. For example, the data processing system may identify posts that contain certain keywords or contain syntax by comparing words or phrases from the posts to a database. The data processing system may identify posts as relevant if certain words or phrases or a threshold number of words or phrases match words or phrases stored in the database. From the relevant posts, the data processing system may identify the authors using name recognition techniques on text in or associated with the posts. In some implementations, in addition to the posts, the data processing system may identify other online interaction data regarding medical entities, such as data related to an online profile (e.g., followers, likes, posts, retweets, shares, and other metadata). The data processing system may then use matching (e.g., exact matching or fuzzy matching) techniques to match the posts or other online interaction data to entity profiles stored by the data processing system. The data processing system may store indications (e.g., pointers to the posts or other online interaction data) in the entity profiles matched to the posts to indicate the match.

At operation 604, the data processing system may calculate online interaction metrics from the matched posts and/or other online interaction data. For example, from the collected online interaction data and for individual profiles, the data processing system may increment one or more counters indicating the number of followers, posts, likes, shares, mentions, etc. The data processing system may also identify other metrics such as the number of re-posts, number of connections, etc., the profiles have. The data processing system may retrieve such data from the respective entity profiles to calculate the metrics.

At operation 606, the data processing system may calculate the influence score for the entity profiles. The data processing system may do so using the metrics calculated in operation 604. In instances in which the data processing system only uses online interaction metrics, the influence score may be a "digital influence" score indicating the influence the different medical entities have online. The data processing system may calculate the influence scores for the different entity profiles with the metrics using an algorithm, such as MDSM TOPSIS. After generating the influence scores, the data processing system may display the influence scores on a user interface, such as a user interface of a computing device being accessed by a user. In some implementations, the data processing system may perform the systems and methods described herein to select key opinion leaders and/or rising stars from the influence scores and present the selected key opinion leaders and/or rising stars in addition to or instead of the influence scores.

Figure 7:
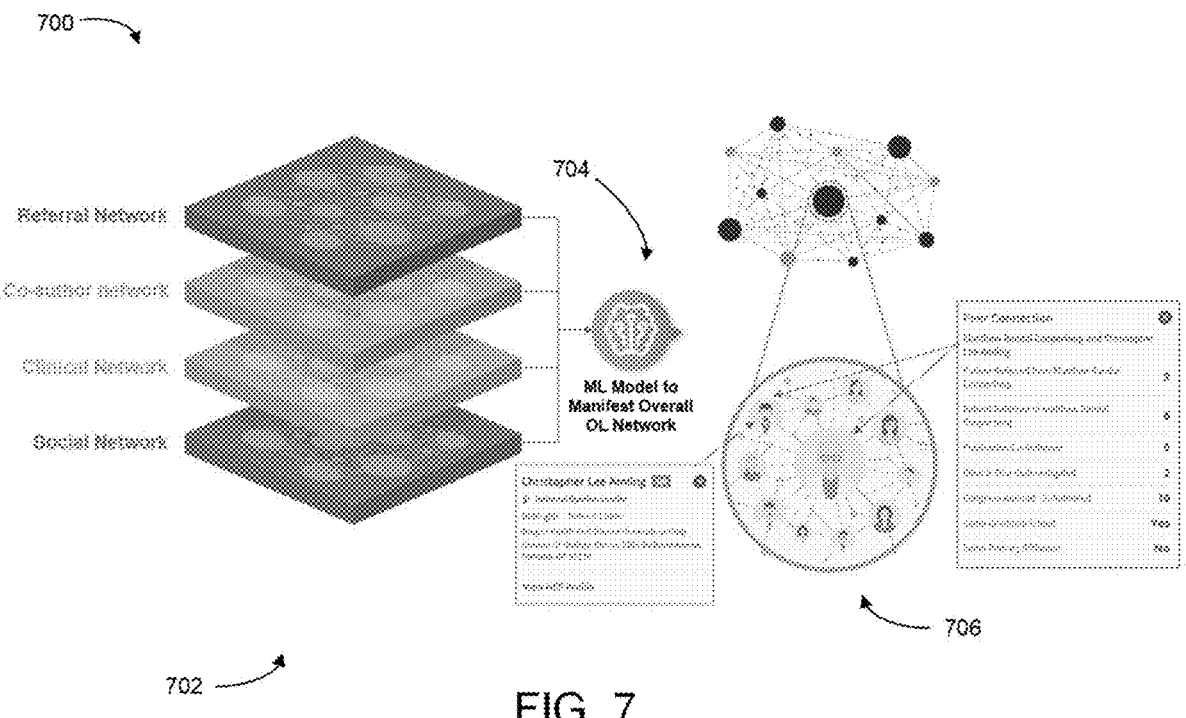
FIG. 7 illustrates another sequence for implementing a multi-model architecture, including a referral network graph, for filtering entity profiles, in accordance with one or more implementations.
Figure 8A:
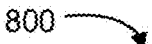
Figure 8B:
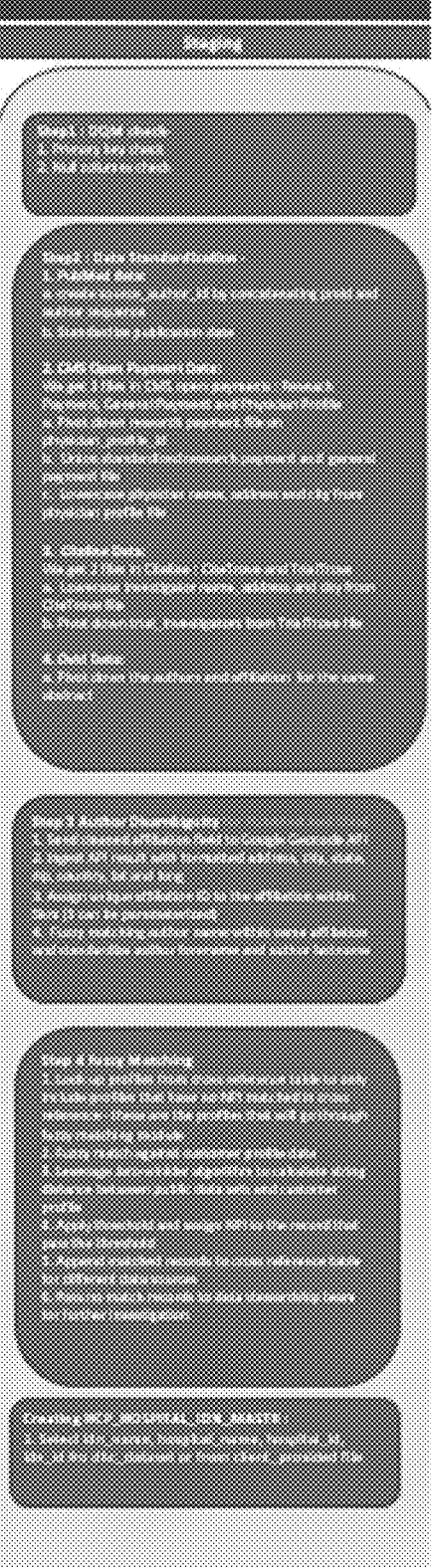
Figure 8C:
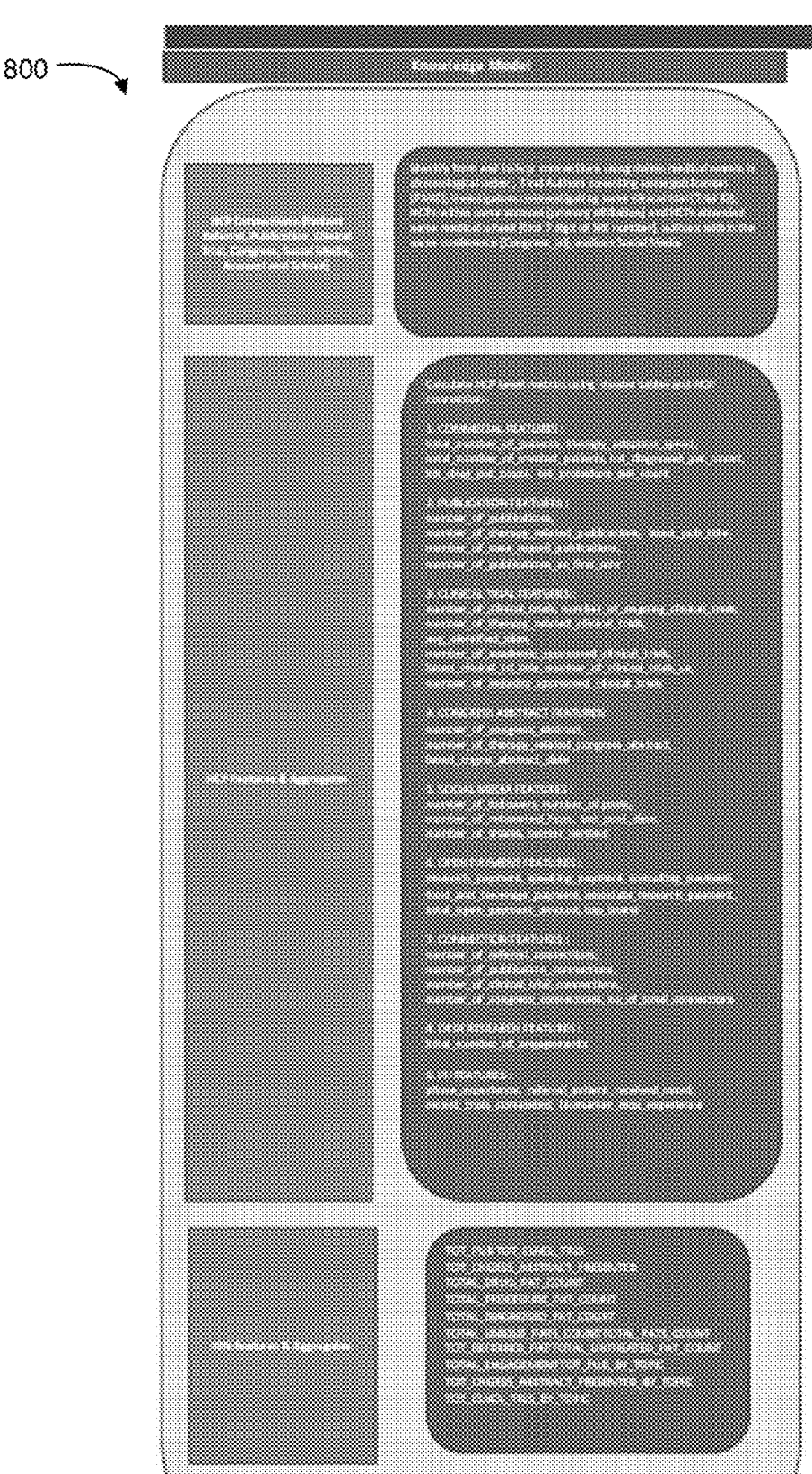
Figure 8D:
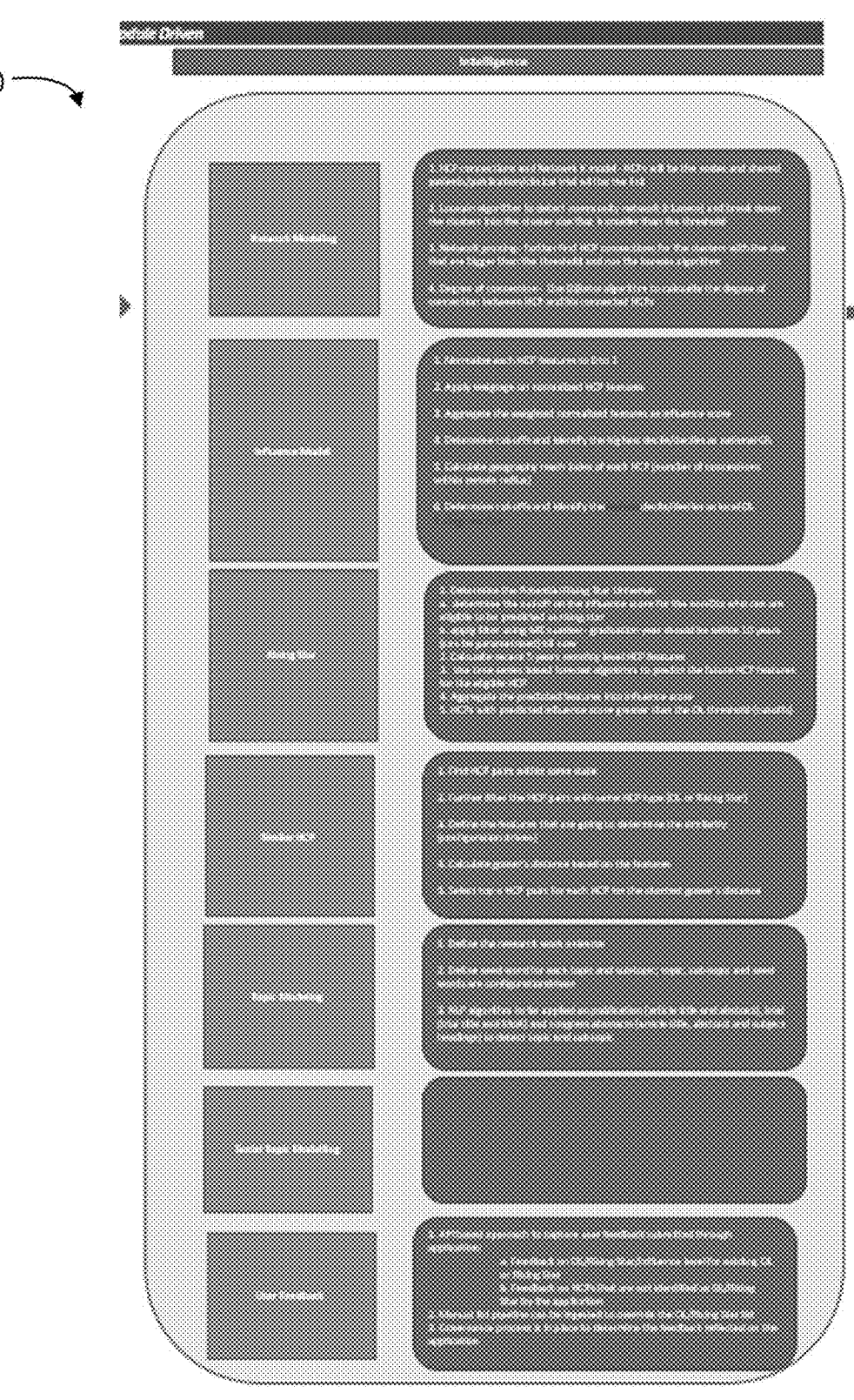

Referring now to FIG. 7, another example sequence 700 of implementing a multi-model architecture, including a referral network graph, for filtering entity profiles is shown, in accordance with one or more implementations. The sequence 700 may be performed by a data processing system (e.g., the profile filtering engine 202, the analytics server 310*a*, a client device 165, or any other computing device). The sequence 700 may include any number of steps and the steps may be performed in any order. In some implementations, performance of the sequence 700 may enable the data processing system to generate influence scores for entity profiles based on online interaction data and clinical data.

At operation 702, the data processing system may generate a network graph data structure from clinical data and/or online interaction data. The data processing system may generate the network graph data structure with layers of connections of different types. For instance, as illustrated, the data processing system may generate the network graph from connections generated from referrals, co-authorship, clinical relationships, and/or social network affiliates. When generating the connections, the data processing system may generate the connections in the profiles of the network graph data structure with identifications of the degrees of the connections, the strength of the connections (e.g., the affinity score), and/or the context of the connections (e.g., the data processing system identified that caused the data processing system to generate the connections).

At operation 704, the data processing system may input data from the network graph data structure into one or more machine learning models or other models. The models may be configured to generate insights into the entity profiles to select the key opinion leaders and/or rising stars. For instance, the data processing system may generate insights 706 regarding a particular entity profile of the network graph data structure using the models. The data processing system may do so by calculating metrics from clinical and/or online interaction data associated with the entity profile (e.g., in which the entity of the entity profile is named). The data processing system may input the metrics into the models to generate an influence score for the entity profile that can be used to determine whether the entity profile is a key opinion leader or a rising star.

Referring now to FIGS. 8A-D, a non-limiting example of a data flow 800 of a system implementing the systems and methods described herein is shown, in accordance with one or more implementations. In the data flow 800, a processor (e.g., a processor of the profile filtering engine 202, the analytics server 310*a*, a client device 165, or any other computing device) may receive a variety of different types of clinical data and online interaction data to select key opinion leaders and/or rising stars.

For example, at operation 802, the processor may receive data from open-source resources (e.g., resources that are available to the public). In doing so, the processor may receive clinical data regarding clinical trials, publications, from Congress, open payments, and/or social media. At operation 804, the processor may perform pre-processing techniques on the clinical data. For example, the processor may perform ad-hoc processing to verify the different clinical and online interaction data has in case a group entity's (e.g., a client's) data is not in the appropriate patient cohort.

At operation 806, the processor may ingest the received data. For instance, the processor may load the data files from the client and ingest data from the open-source sources via one or more APIs. Upon loading all of the data, the processor may perform a quality check removing any duplicate data and/or null values in the data. Data records or files that pass the data quality checks may move ahead for further processing and erroneous records or data files (e.g., records or data files that contain duplicate values and/or null values) may be stored separately in an invalid data file.

At operation 808, the processor may transform the data into a format executable computer models can read. For instance, the processor may standardize the data according to the following set of rules:

1. Flag values are standardized and updated from Yes, No, 0, 1 to Y & N for all applicable fields,
  2. Name fields (For e.g. First name, Last name, City, State, etc.) are standardized to be in upper case, and
  3. Start date and end date for different time buckets (YTD, R12M, etc.) are standardized in a common standard format for metric calculations.

The processor may also match the collected data to entity profiles using exact matching or fuzzy matching techniques.

At operation 810, the processor may perform metric calculations to calculate clinical metrics and/or online interaction metrics. Doing so may, for example, involve maintaining and/or incrementing counters to calculate the following metrics and metric types:

1. COMMERCIAL METRICS: total number of patients, therapy adoption speed, total number of treated patients, total diagnosed patient count, total drug patient count, total procedure patient count;
  2. PUBLICATION METRICS: number of publications, number of therapy related publications, latest publication title, number of case report publications, number of publications as first author;
  3. CLINICAL TRIAL METRICS: number of clinical trials, number of ongoing clinical trials, number of therapy related clinical trials, average identified sites, number of academic sponsored clinical trials, latest clinical trial title, number of clinical trials in the United States, number of industry sponsored clinical trials;
  4. CONGRESS ABSTRACT METRICS: number of congress abstracts, number of therapy related congress abstracts, latest congress abstract date;
  5. SOCIAL MEDIA METRICS: number of followers, number of posts, number of retweeted hcps, last post date, number of shares, twitter verified;
  6. OPEN PAYMENT METRICS: research payment, speaking payment, consulting payment, food and beverage payment, associate research payment, total open payment amount, top brand;
  7. CONNECTION METRICS: number of referral connections, number of publication connections, number of clinical trial connections, number of congress connections, no of total connections;
  8. DESK RESEARCH METRICS: total number of engagements;
  9. PII METRICS: phase experience, referral patient received count, recent trials completed, biomarker moa experience; and
  10. OTHER CLINICAL METRICS: total publications, total clinical trials, total congress abstracts presented, total drug patient count, total procedure patient count, total diagnosed patient count, total unique patients count, total patients count, total referred patient total untreated patient count, total engagement total publications by topic, total congress abstract presented by topic, total clinical trials by topic.

In some implementations, the processor may calculate metrics regarding connections the medical entities may have. For example, the processor may identify connections based on claims of medical events in chronological order, authors co-writing the same publication (PMID), investigators co-investigating the same clinical trial (Trial ID), medical entities within the same account (primary affiliation), medical entities that attended the same medical school (which may be identified from the first seven digit of an ME number in the medical entities respective entity profiles), authors within the same conference (Congress_id), and/or authors that communicate with each over social media websites. The processor may calculate the metrics such as the "connection metrics" as described above from such connections.

At operation 812, the processor may input the data into individual machine learning models and other models to calculate influence scores and select key opinion leaders and/or rising stars from the influence scores. For instance, the processor may implement the systems and methods described herein to calculate influence scores for the individual entity profiles and identify key opinion leaders from a highest segment of the calculated influence scores. The processor may additionally identify rising stars as medical entities that do not currently have influence scores that put them into the key opinion leader segment, but that are on track to be key opinion leaders in the future. The processor may present the list of key opinion leaders and/or rising stars and/or the respective scores that were used to identify them to a user on a user interface.

FIGS. 9A-9C illustrate non-limiting examples of graphical user interfaces 900, 902, and 904 of an electronic platform enabling users to request and view details regarding key opinion leaders and/or rising stars, in accordance with one or more implementations. The user interface 900 illustrates an entity profile of a medical including the user's social media information. A data processing system (e.g., the profile filtering engine 202, the analytics server 310a, a client device 165, or any other computing device) may generate the user interface 900 by retrieving the data from the medical entities profile in memory and displaying the retrieved data on the user interface 900. As illustrated, a user may select different tabs on the user interface to view different types of information about the medical entity. The user interface 902 may include details about the different types of influencers the data processing system calculated in local settings and a geographical region. As illustrated, a user may filter through different settings or regions to view specific details about the influencers that are located or otherwise associated with (e.g., work in) those settings or regions. The user interface 904 may include data about a particular local setting. A user may select different local settings to view the details for each setting.

The foregoing method descriptions and the process flow diagrams are provided merely as illustrative examples and are not intended to require or imply that the steps of the various embodiments must be performed in the order presented. The steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations can be performed in parallel or concurrently. In addition, the order of the operations may be re-arranged. A process may correspond to a method, a function, a procedure, a subroutine, a subprogram, and the like. When a process corresponds to a function, the process termination may correspond to a return of the function to a calling function or a main function.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A method for improved operation of a search engine for identification of entities across heterogeneous data, comprising:

extracting, via one or more application programming interfaces (APIs) and a web scraping engine by a processor from a plurality of data sources and for a plurality of medical entities, clinical data and online interaction data;

generating, by the processor from the clinical data and the online interaction data, a plurality of entity profiles for the plurality of medical entities;

generating, by the processor based on the online interaction data and the clinical data, a network graph data structure of a search engine stored in memory, by:

generating a plurality of node data structures corresponding to the plurality of entity profiles each containing an identification of an entity corresponding to the node data structure;

generating edges between respective pairs of the node data structures indicated by pointers within the respective pairs of node data structures based on the clinical data and the online interaction data indicating relationships between the respective pairs of node data structures; and weighting the edges between the respective pairs of the node data structures according to an affinity score computed according to predefined connection rules applied to co-authorship data, referral data, shared patient data, and social media interactions between the respective pairs of node data structures identified from the clinical data and the online interaction data extracted using the one or more APIs and the web scraping engine;

calculating, by the processor, weighted connection counts by traversing the network graph data structure using the pointers within the pairs of node data structures and one or more clinical metrics and one or more online interaction metrics for the plurality of entity profiles from the clinical data and the online interaction;

executing, by the processor, a machine learning model of the search engine using identifications of the plurality of entity profiles, the weighted connection counts, the one or more clinical metrics, and the one or more online interaction metrics as input to generate influence scores for the plurality of entity profiles;

selecting, by the processor using the search engine, a subset of the plurality of entity profiles responsive to each entity profile of the subset having an influence score satisfying a selection criteria;

ranking, by the processor using the search engine, search results corresponding to the selected subset by the influence score of each entity profile of the subset;

generating, by the processor using the search engine, a structured search results record comprising, for each selected entity profile: a rank position, a corresponding influence score, location information, key metric values, and relationship data from the network graph data structure, wherein the search engine is configured to generate more accurate search results of heterogeneous data extracted using the one or more APIs and the web search engine; and outputting the structured search results record on to a user interface presented at a computing device.

2. The method of claim 1, further comprising:

storing, by the processor, the one or more clinical metrics and the one or more online interaction metrics;

receiving, by the processor, a request identifying a type of metric; and retrieving, by the processor, a stored metric of the one or more clinical metrics or the one or more online interaction metrics responsive to the stored metric having the type of metric identified in the request.

3. The method of claim 1, wherein extracting the clinical data comprises extracting, by the processor, data related to a clinical trial performed by a medical entity of the plurality of medical entities.

4. The method of claim 1, wherein selecting the subset of the plurality of entity profiles comprises:

comparing, by the processor, the influence scores for the plurality of entity profiles; and segmenting, by the processor, the influence scores for the plurality of entity profiles into a plurality of segments based on the comparing, wherein selecting the subset of the plurality of entity profiles comprises selecting, by the processor, the subset responsive to each entity profile of the subset having an influence score within a segment having highest influence scores of the plurality of segments.

5. The method of claim 1, further comprising:

for each of the medical entities and based on the network graph data structure, incrementing, by the processor, a geographic influence counter for each connection the medical entity has with another of the plurality of medical entities having a location within a defined radius of a predetermined location, wherein selecting the subset of the plurality of entity profiles comprises selecting, by the processor, the subset responsive to each entity profile of the subset having a geographic influence counter with a count exceeding a threshold.

6. The method of claim 1, further comprising:

for each of the medical entities and based on the network graph data structure, incrementing, by the processor, a geographic influence counter for each connection the medical entity has with another of the plurality of medical entities having a location within a defined radius of a predetermined location; and segmenting, by the processor, the influence scores for the plurality of entity profiles into a plurality of segments based on the comparing, wherein selecting the subset of the plurality of entity profiles comprises selecting, by the processor, the subset responsive to each entity profile of the subset having an influence score within a segment having highest influence scores of the plurality of segments and a geographic influence counter with a count exceeding a threshold.

7. The method of claim 1, wherein selecting the subset of the plurality of entity profiles comprises selecting, by the processor, the subset in response to each entity profile of the subset having an influence score above a first threshold, the method further comprising:

identifying, by the processor, a second subset of the plurality of entity profiles responsive to each entity profile of the second subset having an influence score below the first threshold and above a second threshold.

8. The method of claim 7, wherein identifying the second subset of the plurality of entity profiles comprises identifying, by the processor, the second subset responsive to each entity profile of the subset comprising a time within a predefined time period.

9. The method of claim 7, further comprising:

identifying, by the processor for the second subset of the plurality of entity profiles, second clinical data and second online interaction data for a predefined time period;

executing, by the processor, the machine learning model based on the second clinical data and the second online interaction data to generate second influence scores for the second subset of the plurality of entity profiles; and selecting, by the processor, a third subset of entity profiles from the second subset of the plurality of entity profiles responsive to each entity profile of the third subset having a second influence score that exceeds the first threshold.

10. The method of claim 9, further comprising:

calculating, by the processor for the second subset of the plurality of entity profiles and for a plurality of time frames within the predefined time period, one or more second clinical metrics and one or more second online interaction metrics; and executing, by the processor, a second model using the one or more second clinical metrics and the one or more second online interaction metrics to generate predicted clinical metrics and predicted online interaction metrics for the second subset of the plurality of entity profiles.

11. A system comprising a server comprising a processor and a non-transitory computer-readable medium containing instructions that when executed by the processor causes the processor to perform operations comprising:

extracting, via one or more application programming interfaces (APIs) and a web scraping engine from a plurality of data sources and for a plurality of medical entities, clinical data and online interaction data;

generating, from the clinical data and the online interaction data, a plurality of entity profiles for the plurality of medical entities;

generating, by the processor based on the online interaction data and the clinical data, a network graph data structure of a search engine stored in memory, by:

generating a plurality of node data structures corresponding to the plurality of entity profiles each containing an identification of an entity corresponding to the node data structure;

generating edges between respective pairs of the node data structures indicated by pointers within the respective pairs of node data structures based on the clinical data and the online interaction data indicating relationships between the respective pairs of node data structures; and weighting the edges between the respective pairs of the node data structures according to an affinity score computed according to predefined connection rules applied to co-authorship data, referral data, shared patient data, and social media interactions between the respective pairs of node data structures identified from the clinical data and the online interaction data extracted using the one or more APIs and the web scraping engine;

calculating weighted connection counts by traversing the network graph data structure using the pointers within the pairs of node data structures and one or more clinical metrics and one or more online interaction metrics for the plurality of entity profiles from the clinical data and the online interaction data;

executing a machine learning model of the search engine using identifications of the plurality of entity profiles, the weighted connection counts, the one or more clinical metrics, and the one or more online interaction metrics as input to generate influence scores for the plurality of entity profiles;

selecting, using the search engine, a subset of the plurality of entity profiles responsive to each entity profile of the subset having an influence score satisfying a selection criteria;

ranking, by the processor using the search engine, search results corresponding to the selected subset by the influence score of each entity profile of the subset; and generating, using the search engine, a structured search results record comprising, for each selected entity profile: a rank position, a corresponding influence score, location information, key metric values, and relationship data from the network graph data structure, wherein the search engine is configured to generate more accurate search results of heterogeneous data extracted using the one or more APIs and the web search engine; and outputting the structured search results record on to a user interface presented at a computing device.

12. The system of claim 11, wherein the operations further comprise:

storing the one or more clinical metrics and the one or more online interaction metrics;

receiving a request identifying a type of metric; and retrieving a stored metric of the one or more clinical metrics or the one or more online interaction metrics responsive to the stored metric having the type of metric identified in the request.

13. The system of claim 11, wherein extracting the clinical data comprises extracting data related to a clinical trial performed by a medical entity of the plurality of medical entities.

14. The system of claim 11, wherein selecting the subset of the plurality of entity profiles comprises:

comparing the influence scores for the plurality of entity profiles; and segmenting the influence scores for the plurality of entity profiles into a plurality of segments based on the comparing, wherein selecting the subset of the plurality of entity profiles comprises selecting the subset responsive to each entity profile of the subset having an influence score within a segment having highest influence scores of the plurality of segments.

15. The system of claim 11, wherein the operations further comprise:

for each of the medical entities and based on the network graph data structure, incrementing a geographic influence counter for each connection the medical entity has with another of the plurality of medical entities having a location within a defined radius of a predetermined location, wherein selecting the subset of the plurality of entity profiles comprises selecting the subset responsive to each entity profile of the subset having a geographic influence counter with a count exceeding a threshold.

16. The system of claim 11, wherein the operations further comprise:

for each of the medical entities and based on the network graph data structure, incrementing a geographic influence counter for each connection the medical entity has with another of the plurality of medical entities having a location within a defined radius of a predetermined location; and segmenting the influence scores for the plurality of entity profiles into a plurality of segments based on the comparing, wherein selecting the subset of the plurality of entity profiles comprises selecting the subset responsive to each entity profile of the subset having an influence score within a segment having highest influence scores of the plurality of segments and a geographic influence counter with a count exceeding a threshold.

17. The system of claim 11, wherein selecting the subset of the plurality of entity profiles comprises selecting the subset in response to each entity profile of the subset having an influence score above a first threshold, the operations further comprising:

identifying a second subset of the plurality of entity profiles responsive to each entity profile of the second subset having an influence score below the first threshold and above a second threshold.

18. The system of claim 17, wherein identifying the second subset of the plurality of entity profiles comprises identifying the second subset responsive to each entity profile of the subset having a date within a predefined time period.

19. The system of claim 17, wherein the operations further comprise:

identifying, for the second subset of the plurality of entity profiles, second clinical data and second online interaction data for a predefined time period;

executing the machine learning model based on the second clinical data and the second online interaction data to generate second influence scores for the second subset of the plurality of entity profiles; and selecting a third subset of entity profiles from the second subset of the plurality of entity profiles responsive to each entity profile of the third subset having a second influence score that exceeds the first threshold.

20. The system of claim 19, wherein the operations further comprise:

calculating, for the second subset of the plurality of entity profiles and for a plurality of time frames within the predefined time period, one or more second clinical metrics and one or more second online interaction metrics; and executing a second model using the one or more second clinical metrics and the one or more second online interaction metrics to generate predicted clinical metrics and predicted online interaction metrics for the second subset of the plurality of entity profiles, wherein executing the model based on the second clinical data and the second online interaction data comprises executing the model using the predicted clinical metrics and the predicted online interaction metrics as input to generate the second influence score.

* * * * *